US008697373B2

(12) United States Patent
Ring et al.

(10) Patent No.: US 8,697,373 B2
(45) Date of Patent: *Apr. 15, 2014

(54) REAGENTS AND METHODS FOR USE IN CANCER DIAGNOSIS, CLASSIFICATION AND THERAPY

(75) Inventors: Brian Z. Ring, Foster City, CA (US); Douglas T. Ross, Burlingame, CA (US); Robert S. Seitz, Hampton Cove, AL (US)

(73) Assignee: Clarient Diagnostic Services, Inc., Aliso Viejo, CA (US)

( * ) Notice: Subject to any disclaimer, the term of this patent is extended or adjusted under 35 U.S.C. 154(b) by 940 days.

This patent is subject to a terminal disclaimer.

(21) Appl. No.: 12/444,007

(22) PCT Filed: Oct. 9, 2007

(86) PCT No.: PCT/US2007/080800
§ 371 (c)(1),
(2), (4) Date: Jan. 25, 2010

(87) PCT Pub. No.: WO2008/043104
PCT Pub. Date: Apr. 10, 2008

(65) Prior Publication Data
US 2010/0143947 A1    Jun. 10, 2010

(51) Int. Cl.
*G01N 33/574* (2006.01)
*G01N 33/577* (2006.01)
*G01N 33/53* (2006.01)
*G01N 33/566* (2006.01)
*G01N 33/567* (2006.01)
*G01N 33/48* (2006.01)
*G01N 33/50* (2006.01)

(52) U.S. Cl.
USPC ........... 435/7.23; 435/7.1; 435/7.2; 435/7.21; 435/960; 435/967; 435/973; 436/501; 436/63; 436/64

(58) Field of Classification Search
USPC ......... 435/7.1, 7.2, 7.21, 7.23, 960, 967, 973; 436/501, 63, 64
See application file for complete search history.

(56) References Cited

U.S. PATENT DOCUMENTS

| 2005/0112622 | A1 | 5/2005 | Ring et al. |
| 2006/0003391 | A1 | 1/2006 | Ring et al. |
| 2006/0063190 | A1 | 3/2006 | Fischer et al. |
| 2007/0065888 | A1* | 3/2007 | Ring et al. ............. 435/7.23 |

FOREIGN PATENT DOCUMENTS

WO    WO-2005/024043 A2    3/2005

OTHER PUBLICATIONS

Baker and Kaprio. Common susceptibility genes for cancer: search for the end of the rainbow. British Medical Journal, 2006. vol. 332, pp. 1150-1152.*
Janssens, Verlinden, Gungor, Raus, and Michiels. Protein biomarkers for breast cancer prevention. European Journal of Cancer Prevention, 2004. vol. 13, pp. 307-317.*
Mc Shane, Altman, Sauerbrei, Taube, Gion, and Clark. REporting recommendations for tumour MARKer prognostic studies (REMARK). European Journal of Cancer, 2005. vol. 41, pp. 1690-1696.*
Andrews, Lake, Popadiuk, and Kao. Requirement of Pygopus 2 in breast cancer. International Journal of Oncology, 2007. vol. 30 No. 2, pp. 357-363.*
Pegram, Konecny, O'Callaghan, Beryt, Pietras, and Slamon. Rational combinations of trastuzumab with chemotherapeutic drugs used in the treatment of breast cancer. Journal of the National Cancer Institute, 2004. vol. 96, pp. 739-749.*
Haab, B. B., Proteomics, 3: 2116-2122, 2003.*
Kakiuchi, S., et al. Molecular Cancer Research, 1: 485-499, 2003.*
AJCC Cancer Staging Manual, Lippincott, 5th Ed., pp. 171-180, 1997.
Alizadeh, et al., "Distinct Types of Diffuse Large B-Cell Lymphoma Identified by Gene Expression Profiling", *Nature*, 403: 503-511, 2000.
Alizadeh, et al., "Towards a novel classification of human malignancies based on gene expression patterns", *J Pathol*; 195(1): 41-52, 2001.
Alon, et al., "Broad Patterns of Gene Expression Revealed by Clustering Analysis of Tumor and Normal Colon Tissues Probed by Oligonucleotide Arrays", *Proc. Natl. Acad. Sci. USA*, 96: 6745-6750, 1999.
Altschul, et al., "Basic local alignment search tool," *J. Mol. Biol.*, 215:403, 1990.
Bartlett, et al., "Mammostrat as a tool to stratify patients at risk of recurrence during endocrine therapy", *Poster at San Antonio Breast Symposium*, 2008.
Beer, et al., "Gene-Expression Profiles Predict Survival of Patients with Lung Adenocarcinoma", *Nature Medicine*, 8(8): 816-824, 2002.
Bhattacharjee, et al., "Classification of Human Lung Carcinomas by mRNA Expression Profiling Reveals Distinct Adenocarcinoma Subclasses", *Proc. Nat. Acad. Sci. USA*, 98: 13790-13795, 2001.
Davies, et al., "Antibody-Antigen Complexes", *Annual Rev. Biochem.*, 59:439, 1990.
Dhanasekaran, et al., "Delineation of Prognosis Biomarkers in Prostate Cancer", *Nature*, 412:822-826, 2001.
Di Leo, et al., "Predictive Molecular Markers in the Adjuvant Therapy of Breast Cancer: State of the Art in the Year 2002", *Int. J. Clin. Oncol.* 7: 245-253, 2002.
Dim, et al., "Expression of a Novel Cell-cycle Regulated Protein HTF9C, Identifies a Subgroup of HER2 Positive Breast Cancer with a More Aggressive Clinical Course," *Modern Pathology*, 20:28A-29A, 2007.

(Continued)

*Primary Examiner* — Alana Harris Dent
*Assistant Examiner* — Anne Holleran
(74) *Attorney, Agent, or Firm* — Charles E. Lyon; Robert N. Sahr; Choate, Hall & Stewart LLP

(57) ABSTRACT

Methods and reagents for classifying HER2+ breast tumors and for identifying new HER2+ breast tumor classes and subclasses. Methods for correlating tumor class or subclass with therapeutic regimen or outcome, for identifying appropriate (new or known) therapies for particular classes or subclasses, and for predicting outcomes based on class or subclass. New therapeutic agents and methods for the treatment of HER2+ breast cancer.

15 Claims, 7 Drawing Sheets

(56) References Cited

OTHER PUBLICATIONS

Ferrando, et al., "Gene Expression Signatures Define Novel Oncogenic Pathways in T Cell Acute Lymphoblastic Leukemia" *Cancer Cell*, 1: 75-87, 2002.

Finlin, et al., "RERG is a novel ras-related, estrogen-regulated and growth-inhibitory gene in breast cancer", *J Biol Chem*, 276(45): 42259-67, 2001.

Garber, et al., "Diversity of Gene Expression in Adenocarcinoma of the Lung", *Proc. Natl. Acad. Sci. USA*, 98: 13784-13789, 2001.

Gruvberger, et al., "Estrogen Receptor Status in Breast Cancer is Associated with Remarkably Distinct Gene Expression Patterns", *Cancer Res*. 61: 5979-5984, 2001.

Gusterson, et al., "Basal cytokeratins and their relationship to the cellular origin and functional classification of breast cancer", *Breast Cancer Research*, 7: 143-148, 2005.

Hanker, et al., "Tools to study the function of the Ras-related, estrogen-regulated growth inhibitor in breast cancer", *Methods Enzymol*, 439: 53-72, 2008.

Hayes, et al., "Prognosis Factors in Breast Cancer: Current and New Predictors of Metastasis" *J. Mamm. Gland Bio. Neo*. 6: 375-392, 2001.

Hayes, et al., "Tumor Marker Utility Grading System: a Framework to Evaluate Clinical Utility of Tumor Markers" *J. Natl Cancer Inst*.. 88: 1456-1466, 1996.

Hedenfalk, et al., "Gene-Expression Profiles in Hereditary Breast Cancer", *N.EngL. J. Med*. 344: 539-548, 2001.

Hippo, et al., "Global Gene Expression Analysis of Gastric Cancer by Oligonucleotide Microarrays", *Cancer Res*. 62: 233-240, 2002.

Hofmann, et al., "Relation Between Resistance of Philadelphia-Chromosome-Positive Acute Lymphoblastic Leukaemia to the Tyrosine Kinase Inhibitor ST1571 and Gene-Expression Profiles: A Gene-Expression Study" *Lancet*, 359: 481-486, 2002.

Hopp, et al., "A computer program for predicting protein antigenic determinants," *Mol. Immunol*., 20:483, 1983.

Hopp, et al., "Prediction of Protein Antigenic Determinant of Amino Acid Sequence," *Proc. Nat. Acad. Sci*., 78:3824, 1981.

International Search Report, PCT/US2007/080800, mailed on Jun. 4, 2008.

Jazaeri, et al., "Gene Expression Profiles of BRCAI-Linked, BRCA-2-Linked, and Sporadic Ovarian Cancers", *J. Natl Cancer Inst*. 94: 990-1000, 2002.

Jensen, et al., "Characterization of a novel anti-fatty acid synthase (FASN) antiserum in breast tissue", Mod Pathol, 21(12): 1413-20, 2008.

Krogh, et al., "Predicting transmembrane protein topology with a hidden Markov model: application to complete genomes," *J. Mol. Biol*., 305:567, 2001.

LaTulippe, et al., "Comprehensive Gene Expression Analysis of Prostate Cancer Reveals Distinct Transcriptional Programs Associated with Metastatic Disease", *Cancer Res*. 62: 4499-4506, 2002.

Lin, et al., "Molecular Diagnosis of Colorectal Tumors by Expression Profiles of 50 GenesExpressed Differentially in Adenomas and Carcinomas", *Oncogene*, 21: 4120-4128, 2002.

MacDonald, et al., "Expression Profiling of Medulloblastoma: PDGFRA and the RAS/MAPKPathway as Therapeutic Targets for Metastatic Disease" *Nature Genet*. 29: 143-152, 2001.

NIH National Institutes of Health Consensus Development Conference Statement: Adjuvant Therapy for Breast Cancer, Nov. 1-3, 2000, *J. Nat. Cancer Inst. Monographs*, 30: 5-15, 2001.

Perou, et al., "Distinctive gene expression patterns in human mammary epithelial cells and breast cancers", *Proc Natl Acad Sci USA*, 96(16): 9212-7, 1999.

Perou, et al., "Molecular Portraits of Human Breast Tumours" *Nature*, 406: 747-752, 2000.

Pomeroy, et al., "Prediction of Central Nervous System Embryonal Tumour Outcome Based on Gene Expression", *Nature*, 415: 436-442, 2002.

Ravdin, et al., "A Demonstration that Breast Cancer Recurrence can be Predicted by Neural Network Analysis", *Breast Cancer Res. Treat*. 21: 47-53, 1992.

Ring et al., "Novel prognostic immunohistochemical biomarker panel for estrogen receptor-positive breast cancer", Journal of Clinical Oncology, 24;19: 3039-3047, 2006.

Ring, et al., "Gene expression patterns within cell lines are predictive of chemosensitivity", *BMC Genomics*, 9: 74, 2008.

Ring, et al., "Gene expression patterns within cell lines are predictive of chemosensitivity", *Poster at American Association of Cancer Research*, 2006.

Ring, et al., "Microarrays and molecular markers for tumor classification", *Genome Biology*, 3(5): 3-6, 2002.

Rosenwald, et al., "The Use of Molecular Profiling to Predict Survival After Chemotherapy for Diffuse Large-B-Cell Lymphoma", *N. Engl. J. Med*. 346: 1937, 2002.

Ross, et al., "A comparison of gene expression signatures from breast tumors and breast tissue derived cell lines", *Dis Markers*, 17(2): 99-109, 2001.

Ross, et al., "A novel prognostic immunohistochemical biomarker panel for estrogen receptor expressing breast cancer", *Poster at San Antonio Breast Cancer Symposium*, 2005.

Ross, et al., "Chemosensitivity and stratification by a five monoclonal antibody IHC test in the NSABP B20 trial", *Poster at ASCO*, 2007.

Ross, et al., "Chemosensitivity and stratification by a five monoclonal antibody immunohistochemistry test in the NSABP B14 and B20 trials", *Clin Cancer Res*, 14(20): 6602-9, 2008.

Ross, et al., "Prognosis and chemosensitivity using a five monoclonal antibody IHC test in a node negative, tamoxifen-treated, ER + breast cancer—NSABP B14 and B20 trials", *Poster at the ASCO Breast Cancer Symposium*, 2007.

Ross, et al., "Systematic variation in gene expression patterns in human cancer cell lines", *Nat Genet*, 24(3): 227-35, 2000.

Ross, et al., "Translating gene expression patterns into IHC diagnostics for breast cancer: novel IHC reagents predict recurrence in a retrospective cohort at the Comprehensive Cancer Institute of Huntsville", *Poster at San Antonio Breast Cancer Symposium*, 2004.

Ross, et al., "Validation of a five reagent immunohistochemistry assay for prognostication of estrogen-receptor expressing breast cancer", *Poster at American Society of Clinical Oncology*, 2006.

Ross, et al., "Validation of a prognostic algorithm based upon a five monoclonal antibody immunohistochemistry test in Tamoxifen-treated, node negative breast cancer: NSABP B14 and B20 studies", *Poster at San Antonio Breast Cancer Symposium*, 2006.

Rost, et al., "Conservation and prediction of solvent accessibility in protein families," *Proteins*, 20:216, 1994.

Russnes, et al., "Translation of breast cancer gene expression profiles into an immunohistochemistry-based classifer", *Poster at the American Association for Cancer Research (AACR) Annual Meeting*, 2007.

Scherf, et al., "A gene expression database for the molecular pharmacology of cancer", *Nat Genet*, 24(3): 236-44, 2000.

Segal, et al., "A Comparison of Estimated Proportional Hazards Models and Regression Trees", *Stat. Med*. 8: 539, 550, 1989.

Seitz, et al., "A Five Antibody Prognostic IHC Test Identifies Estrogen Receptor Positive Patients Classified as Luminal B at High Risk for Tumor Progression", *Poster at the American Association for Cancer Research (AACR) Annual Meeting*, 2007.

Seitz, et al., "An Immunohistochemical Panel of Antibodies that Predicts Recurrence in Estrogen Receptor Positive Breast Cancer Patients Correlates with Luminal B Gene Expression Subtype," *Proceedings of the American Association for Cancer Research Annual Meeting*, 48:1202, 2007.

Seitz, et al., "Translation of gene expression patterns into immunohistochemistry biomarkers", *Poster at American Association of Cancer Research*, 2006.

Seitz, et al., "Validation of an Immunohistochemical Biomarker for Identifying Her2+ Patients at High Risk of Recurrence," *Breast Cancer Research and Treatment*, 106:S248, 2007.

Shipp, et al., "Diffuse Large B-Cell Lymphoma Outcome Prediction by Gene-Expression Profiling and Supervised Machine Learning", *Nature Med*., 8: 68-74, 2002.

Singh, et al., "Gene Expression Correlates of Clinical Prostate Cancer Behavior", *Cancer Cell*, 1: 203-209, 2002.

(56) References Cited

OTHER PUBLICATIONS

Sorlie, et al., "Gene Expression Patterns of Breast Carcinomas Distinguish Tumor Subclasses with Clinical Implications", *Proc. Natl. Acad. Sci. USA*, 98: 10869-10874, 2001.

Takahashi, et al., "Gene Expression Profiling of Clear Cell Renal Cell Carcinoma: Gene Identification and Prognostic Classification" *Proc. Natl. Acad. Sci. USA*, 98: 9754-9759, 2001.

Titus, Karen "Reclassifying cancer, guided by genomics", *College of American Pathologists*, 2001.

van de Rijn, et al., "Expression of cytokeratins 17 and 5 identifies a group of breast carcinomas with poor clinical outcome", *Am J Pathol*, 161(6): 1991-6, 2002.

Van't Veer, et al., "Gene Expression Profiling Predicts Clinical Outcome of Breast Cancer" *Nature*, 415: 530-536, 2002.

Wang, et al., "Monitoring Gene Expression Profile Changes in Ovarian Carcinomas Using cDNA Microarray", *Gene*, 229: 101-108, 1999.

Welsh, et al., "Analysis of Gene Expression Profiles in Normal and Neoplastic Ovarian Tissue Samples Identifies Candidate Molecular Markers of Epithelial Ovarian Cancer", *Proc. NatL Acad. Sci. USA*, 98: 1176-1181, 2001.

West, et al., "Predicting the Clinical Status of Human Breast Cancer by Using Gene Expression Profiles" *Proc. Natl. Acad. Sci. USA*, 98: 11462-11467, 2001.

Written Opinion, PCT/US2007/080800, mailed on Jun. 4, 2008.

Yeoh, et al., "Classification, Subtype Discovery, and Prediction of Outcome in Pediatric Acute Lymphoblastic Leukemia by Gene Expression Profiling", *Cancer Cell*, 1: 133-143, 2002.

Zou, et al., "Application of cDNA Microarrays to Generate a Molecular Taxonomy Capable of Distinguishing Between Colon Cancer and Normal Colon", *Oncogene* 21: 4855-4862, 2002.

\* cited by examiner

FIGURE 1

HTF9C HpaII tiny fragments locus 9C [ Homo sapiens ]

GeneID: 27037

Summary

Gene description
    HpaII tiny fragments locus 9C
Primary source
    Ensembl:ENSG00000099899
See related
    HPRD:13719; MIM:611151
Gene type
    protein coding
RefSeq status
    Validated
Organism
    Homo sapiens
Lineage
    Eukaryota; Metazoa; Chordata; Craniata; Vertebrata; Euteleostomi; Mammalia; Eutheria;
    Euarchontoglires; Primates; Haplorrhini; Catarrhini; Hominidae; Homo
Also known as
    HTF9C; MGC102728

Genomic context chromosome: 22; Locations: 22q11.1-22q13; 22q11.21

Additional Links

- MIM 611151
- HPRD 13719
- UniGene Hs.693640

FIGURE 1 (continued)

Related Sequences

| Nucleotide | | Protein |
|---|---|---|
| Genomic | AC006547.9 (72905..78275, complement) | None |
| Genomic | CH471176.2 | EAX02995.1 |
| | | EAX02996.1 |
| | | EAX02997.1 |
| mRNA | AI539558.1 | None |
| mRNA | AK025106.1 | BAB15067.1 |
| mRNA | AK057029.1 | BAB71349.1 |
| mRNA | BC013352.2 | AAH13352.2 |
| mRNA | BC017184.2 | AAH17184.2 |
| mRNA | BC108251.1 | AAI08252.1 |
| mRNA | BI756672.1 | None |
| mRNA | BX349507.2 | None |
| mRNA | CR456354.1 | CAG30240.1 |
| mRNA | CR592601.1 | None |
| mRNA | CR595584.1 | None |
| mRNA | CR608558.1 | None |
| mRNA | CR617494.1 | None |
| mRNA | CR625115.1 | None |

| Protein Accession | Links | |
|---|---|---|
| Q8IZ69 | GenPept | UniProtKB/Swiss-Prot |

FIGURE 2

ERBB2 v-erb-b2 erythroblastic leukemia viral oncogene homolog 2, neuro/glioblastoma derived oncogene homolog (avian) [ Homo sapiens ]

GeneID: 2064

Summary

Official Symbol
    ERBB2
Official Full Name
    v-erb-b2 erythroblastic leukemia viral oncogene homolog 2, neuro/glioblastoma derived oncogene homolog (avian)
Primary source
    HGNC:3430
See related
    Ensembl:ENSG00000141736; HPRD:01281; MIM:164870
Gene type
    protein coding
RefSeq status
    Reviewed
Organism
    Homo sapiens
Lineage
    Eukaryota; Metazoa; Chordata; Craniata; Vertebrata; Euteleostomi; Mammalia; Eutheria;
    Euarchontoglires; Primates; Haplorrhini; Catarrhini; Hominidae; Homo
Also known as
    NEU; NGL; HER2; TKR1; HER-2; c-erb B2; HER-2/neu
Summary
    This gene encodes a member of the epidermal growth factor (EGF) receptor family of receptor tyrosine kinases. This protein has no ligand binding domain of its own and therefore cannot bind growth factors. However, it does bind tightly to other ligand-bound EGF receptor family members to form a heterodimer, stabilizing ligand binding and enhancing kinase-mediated activation of downstream signalling pathways, such as those involving mitogen-activated protein kinase and phosphatidylinositol-3 kinase. Allelic variations at amino acid positions 654 and 655 of isoform a (positions 624 and 625 of isoform b) have been reported, with the most common allele, Ile654/Ile655, shown here. Amplification and/or overexpression of this gene has been reported in numerous cancers, including breast and ovarian tumors. Alternative splicing results in several additional transcript variants, some encoding different isoforms and others that have not been fully characterized.

Genomic context chromosome: 17; Locations: 17q11.2-q12; 17q21.1 See ERBB2 in MapViewer Additional Links

- MIM 164870
- PharmGKB PA27844
- HPRD 01281
- Catalogue of Somatic Mutations in Cancer (COSMIC) Catalogue of Somatic Mutations in Cancer (COSMIC)
- UniGene Hs.446352

FIGURE 2 (continued)

Related Sequences

| Nucleotide | | Protein |
|---|---|---|
| Genomic | AB025285.1 | None |
| Genomic | AB221349.1 | BAE15959.1 |
| Genomic | AB221350.1 | BAE15960.1 |
| Genomic | AC079199.9 (71077..73120) | None |
| Genomic | AC087491.5 (118738..157216) | None |
| Genomic | AY208911.1 | AAO18082.1 |
| Genomic | CH471152.1 | EAW60595.1 |
| | | EAW60596.1 |
| | | EAW60597.1 |
| Genomic | L29395.1 | AAA35809.1 |
| Genomic | M11767.1 | AAA35808.1 |
| Genomic | M12036.1 | AAA35978.1 |
| Genomic | M16792.1 | AAA58637.1 |
| Genomic | M86910.1 | AAF30295.1 |
| Genomic | M95667.1 | AAC37531.1 |
| mRNA | AB025286.1 | None |
| mRNA | AF177761.2 | AAD56009.2 |
| mRNA | AK131568.1 | BAD18701.1 |
| mRNA | BC080193.1 | None |
| mRNA | BC110392.1 | None |
| mRNA | BI755753.1 | None |
| mRNA | BM678576.1 | None |
| mRNA | CN409735.1 | None |
| mRNA | CR591377.1 | None |
| mRNA | CR592336.1 | None |
| mRNA | M11730.1 | AAA75493.1 |
| mRNA | X03363.1 | CAA27060.1 |

| Protein Accession | Links | |
|---|---|---|
| P04626 | GenPept | UniProtKB/Swiss-Prot |
| Q4H1F1 | GenPept | UniProtKB/TrEMBL |
| Q4H1F2 | GenPept | UniProtKB/TrEMBL |
| Q6ZMM4 | GenPept | UniProtKB/TrEMBL |
| Q8WYV0 | GenPept | UniProtKB/TrEMBL |
| Q9NP09 | GenPept | UniProtKB/TrEMBL |
| Q9UK79 | GenPept | UniProtKB/TrEMBL |

FIGURE 3

ESR1 estrogen receptor 1 [ Homo sapiens ]

GeneID: 2099

Official Symbol
 ESR1
Official Full Name
 estrogen receptor 1
Primary source
 HGNC:3467
Locus tag
 RP1-130E4.1
See related
 Ensembl:ENSG00000091831; HPRD:00589; MIM:133430
Gene type
 protein coding
RefSeq status
 Provisional
Organism
 Homo sapiens
Lineage
 Eukaryota; Metazoa; Chordata; Craniata; Vertebrata; Euteleostomi; Mammalia; Eutheria;
 Euarchontoglires; Primates; Haplorrhini; Catarrhini; Hominidae; Homo
Also known as
 ER; ESR; Era; ESRA; NR3A1; DKFZp686N23123
Summary
 The estrogen receptor (ESR) is a ligand-activated transcription factor composed of several
 domains important for hormone binding, DNA binding, and activation of transcription. Alternative
 splicing results in several ESR1 mRNA transcripts, which differ primarily in their 5-prime
 untranslated regions. The translated receptors show less variability.[supplied by OMIM]

Genomic context chromosome: 6; Location: 6q25.1 See ESR1 in MapViewer

Additional Links

- MIM 133430
- PharmGKB PA156
- HPRD 00589
- UniGene Hs.208124
- UniGene Hs.652547

FIGURE 3 (continued)

Related Sequences

| | Nucleotide | Protein |
|---|---|---|
| Genomic | AF123500.1 | AAD52984.1 |
| Genomic | AF326912.1 | AAG42501.1 |
| Genomic | AL049821.6 | CAI22123.1 |
| Genomic | AL078582.13 | CAI42285.1 |
| Genomic | AL356311.6 | CAI21011.1 |
| | | CAI21012.1 |
| Genomic | AL590993.14 | CAI14237.1 |
| Genomic | AY425004.1 | AAQ91815.1 |
| Genomic | CH471051.2 | EAW47740.1 |
| | | EAW47741.1 |
| Genomic | X62462.1 | CAA44322.1 |
| mRNA | AF120105.1 | AAD23565.1 |
| mRNA | AF258449.1 | AAG41358.1 |
| mRNA | AF258450.1 | AAG41359.1 |
| mRNA | AF258451.1 | AAG41360.1 |
| mRNA | AY750962.1 | AAW69860.1 |
| mRNA | BC128573.1 | AAI28574.1 |
| mRNA | BC128574.1 | AAI28575.1 |
| mRNA | BX640939.1 | CAE45969.1 |
| mRNA | M12674.1 | AAA52399.1 |
| mRNA | M69297.1 | AAA58462.1 |
| mRNA | U47678.1 | AAB00115.1 |
| mRNA | U68067.1 | AAC51874.1 |
| mRNA | U68068.1 | AAC51875.1 |
| mRNA | X03635.1 | CAA27284.1 |
| mRNA | X73067.1 | CAA51528.1 |
| mRNA | Z75126.1 | CAA99436.1 |

| Protein Accession | Links | |
|---|---|---|
| P03372 | GenPept | UniProtKB/Swiss-Prot |
| Q14267 | GenPept | UniProtKB/TrEMBL |
| Q14268 | GenPept | UniProtKB/TrEMBL |
| Q5C8S5 | GenPept | UniProtKB/TrEMBL |
| Q5TFI3 | GenPept | UniProtKB/TrEMBL |
| Q6MZQ9 | GenPept | UniProtKB/TrEMBL |
| Q9H1Z6 | GenPept | UniProtKB/TrEMBL |
| Q9H2M1 | GenPept | UniProtKB/TrEMBL |
| Q9H2M2 | GenPept | UniProtKB/TrEMBL |
| Q9UBT1 | GenPept | UniProtKB/TrEMBL |
| Q9UE35 | GenPept | UniProtKB/TrEMBL |
| Q9Y2W8 | GenPept | UniProtKB/TrEMBL |

# REAGENTS AND METHODS FOR USE IN CANCER DIAGNOSIS, CLASSIFICATION AND THERAPY

BACKGROUND OF THE INVENTION

A major challenge of cancer treatment is the selection of therapeutic regimens that maximize efficacy and minimize toxicity for a given patient. A related challenge lies in the attempt to provide accurate diagnostic, prognostic and predictive information. At present, tumors are generally classified under the tumor-node-metastasis (TNM) system. This system, which uses the size of the tumor, the presence or absence of tumor in regional lymph nodes, and the presence or absence of distant metastases, to assign a stage to the tumor is described in the *AJCC Cancer Staging Manual*, Lippincott, 5th ed., pp. 171-180 (1997). The assigned stage is used as a basis for selection of appropriate therapy and for prognostic purposes. In addition to the TNM parameters, morphologic appearance is used to further classify tumors into tumor types and thereby aid in selection of appropriate therapy. However, this approach has serious limitations. Tumors with similar histopathologic appearance can exhibit significant variability in terms of clinical course and response to therapy. For example, some tumors are rapidly progressive while others are not. Some tumors respond readily to hormonal therapy or chemotherapy while others are resistant.

Assays for cell surface markers, e.g., using immunohistochemistry, have provided means for dividing certain tumor types into subclasses. For example, one factor considered in prognosis and treatment decisions for breast cancer is the presence or absence of the estrogen receptor (ER) in tumor samples. ER-positive breast cancers typically respond much more readily to hormonal therapies such as tamoxifen, which acts as an anti-estrogen in breast tissue, than ER-negative tumors. Though useful, these analyses only in part predict the clinical behavior of breast tumors. There is phenotypic diversity present in cancers that current diagnostic tools fail to detect. As a consequence, there is still much controversy over how to stratify patients amongst potential treatments in order to optimize outcome (e.g., for breast cancer see "NIH Consensus Development Conference Statement: Adjuvant Therapy for Breast Cancer, Nov. 1-3, 2000", *J. Nat. Cancer Inst. Monographs*, 30:5-15, 2001 and Di Leo et al., *Int. J. Clin. Oncol.* 7:245-253, 2002).

For example, the over-expression of the HER2 protein in a subset of breast cancers (HER2+) is associated with higher grade tumors that are more likely to demonstrate nodal involvement and decreased survival. Despite these distinctive clinicopathologic features, significant heterogeneity exists among patients with HER2+ disease with roughly half of these tumors expressing steroid hormone receptors, as well as demonstrating varying degrees of responsiveness to Trastuzumab (Herceptin™) targeted therapy. The identification of additional factors that could help better define the clinical diversity of HER2+ tumors would benefit therapeutic decision-making and suggest new molecular targets to overcome Trastuzumab (Herceptin™) resistance.

There clearly exists a need for improved methods and reagents for classifying tumors. Once these methods and reagents are available, clinical studies can be performed that will allow the identification of classes or subclasses of patients having different prognosis and/or responses to therapy. Such prognostic tools will allow more rationally based choices governing the aggressiveness of therapeutic interventions; such predictive tools will also be useful for directing patients into appropriate treatment protocols.

SUMMARY OF THE INVENTION

The inventors have shown that the marker HTF9C (HpaII tiny fragments locus 9C) binds differentially to tumor samples from different HER2-positive (HER2+) breast cancers. In one aspect, the present invention provides methods of using the HTF9C marker to classify HER2+ breast tumors. In general, the HTF9C marker can be used in conjunction with another marker (e.g., the ER marker) to further classify the tumors.

The inventors have also shown that the HTF9C is a strong predictor of prognosis in patients with HER2+ breast cancers. Thus, in another aspect, the present invention provides methods of using the HTF9C marker to predict the prognosis of patients with HER2+ breast cancer. In general, the HTF9C marker can be used in conjunction with another marker to improve the level of prediction. For example, the HTF9C marker may be used in conjunction with the ER marker which is anti-correlated with the HTF9C marker in HER2+ patients.

In yet another aspect, the present invention provides methods of using the HTF9C marker to predict the likelihood that a patient with HER2+ breast cancer will respond to a particular therapy (e.g., an agent that targets the HER2 protein such as Trastuzumab (Herceptin™); an agent that targets another member of the HER family of proteins such as EGFR/HER1, HER3, HER4, etc.; a cytotoxic agent; or a combination thereof). Again, the HTF9C marker can be used in conjunction with another marker (e.g., the ER marker) to improve the level of prediction.

The invention further provides kits for detecting the HTF9C, HER2 and/or ER markers, new therapeutic agents (e.g., an antibody directed to HTF9C optionally associated with a cytotoxic agent) and methods for the treatment of HER2+ breast cancers.

In general the inventive methods can be practiced with any tumor sample binding agent that recognizes the marker in question ("interaction partner"). In one embodiment the interaction partners are antibodies.

BRIEF DESCRIPTION OF THE APPENDIX

This patent application refers to material comprising a table and data presented as Appendix A. Specifically, Appendix A is a table that lists a variety of biomarkers that could be used in a prognostic or predictive panel in conjunction with the HTF9C marker. The table includes the antibody ID, parent gene name, Entrez Gene ID, known aliases for the parent gene, peptides that were used in preparing antibodies and exemplary antibody titer for staining Using the parent gene name, Entrez Gene ID and/or known aliases for the parent gene, a skilled person can readily obtain the nucleotide (and corresponding amino acid) sequences for each and every one of the parent genes that are listed in Appendix A from a public database (e.g., GenBank, Swiss-Prot or any future derivative of these). The nucleotide and corresponding amino acid sequences for each and every one of the parent genes that are listed in Appendix A are hereby incorporated by reference from these public databases. Antibodies with AGI IDs that begin with s5 or s6 were obtained from commercial sources as indicated.

BRIEF DESCRIPTION OF THE DRAWING

FIG. 1 is a print out from the NCBI website which provides information (e.g., genomic context, sequences, aliases) regarding the HTF9C marker (Entrez Gene ID 27037).

FIG. 2 is a print out from the NCBI website which provides information (e.g., genomic context, sequences, aliases) regarding the HER2 marker (Entrez Gene ID 2064).

FIG. 3 is a print out from the NCBI website which provides information (e.g., genomic context, sequences, aliases) regarding the ER marker (Entrez Gene ID 2099).

DEFINITIONS

Figure 4:
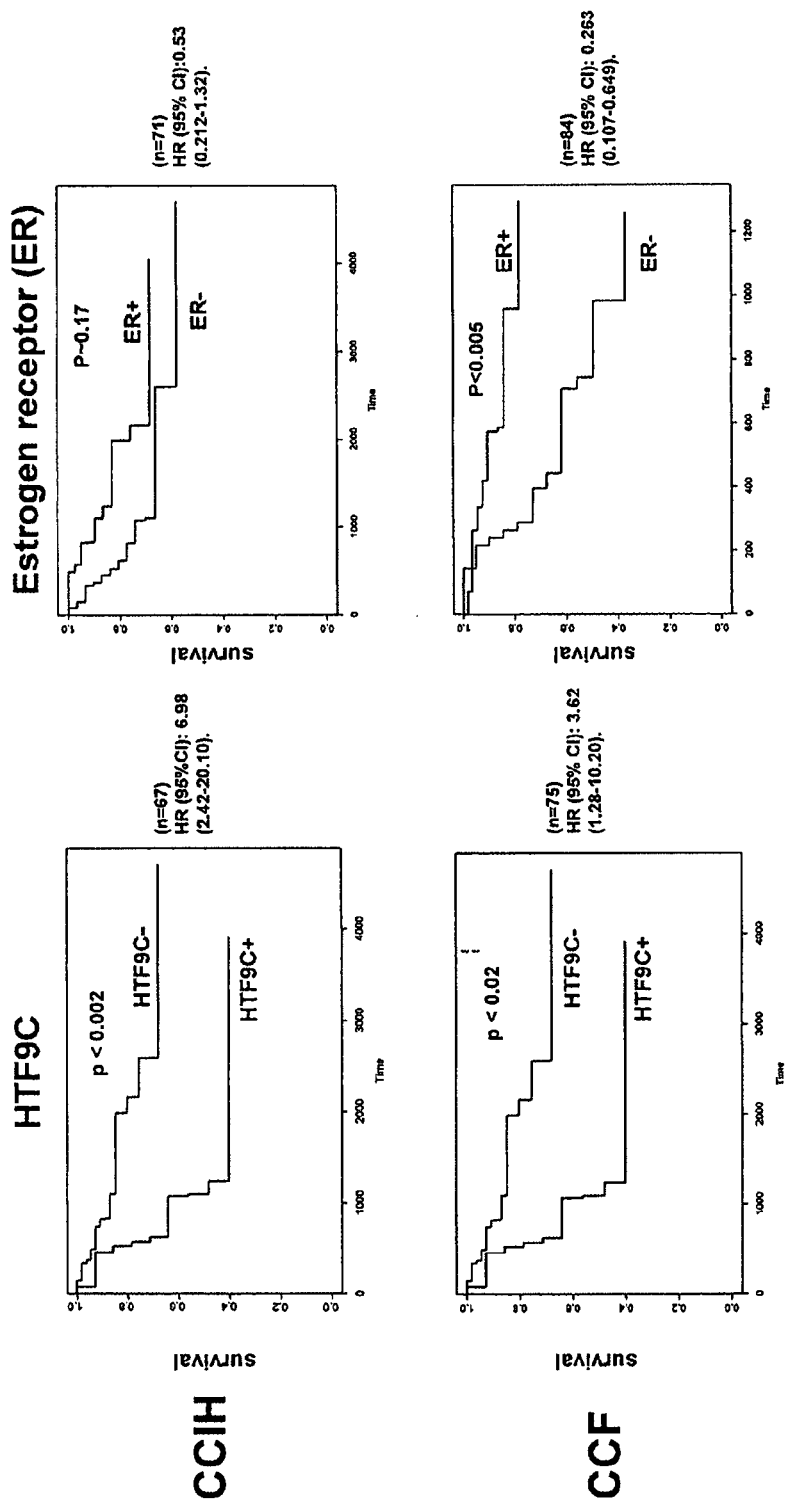
FIG. 4 shows Kaplan-Meier curves that were generated for HER2+ patients in two breast cancer cohorts (CCIH and CCF) after prognostic classification based on (A) staining with an antibody raised against the HTF9C marker and (B) staining with an antibody raised against the ER marker. In each case the patients were placed into one of two prognostic groups, namely "good" (top curve) and "poor" (bottom curve). The CCIH cohort was used to determine the prognostic ability of various tumor markers using univariate association of IHC staining with clinical outcome. HTF9C was identified as a strong prognosticator and this association was then tested on the CCF cohort. As shown in the Figure, HTF9C shows a stronger and more consistent prognostic correlation than the ER marker. In addition, the HTF9C and ER markers are anti-correlated in HER2+ patients (HTF9C is associated with poor outcome while ER is associated with good outcome).

Associated—When an interaction partner and a tumor marker are physically "associated" with one another as described herein, they are linked by direct non-covalent interactions. Desirable non-covalent interactions include those of the type which occur between an immunoglobulin molecule and an antigen for which the immunoglobulin is specific, for example, ionic interactions, hydrogen bonds, van der Waals interactions, hydrophobic interactions, etc. The strength, or affinity of the physical association can be expressed in terms of the dissociation constant ($K_d$) of the interaction, wherein a smaller $K_d$ represents a greater affinity. The association properties of selected interaction partners and tumor markers can be quantified using methods well known in the art (e.g., see Davies et al., *Annual Rev. Biochem.* 59:439, 1990).

Classification panel—A "classification panel" of interaction partners is a set of interaction partners whose collective pattern of binding or lack of binding to a tumor sample, when taken together, is sufficient to classify the tumor sample as a member of a particular class or subclass of tumor, or as not a member of a particular class or subclass of tumor.

Correlation—"Correlation" refers to the degree to which one variable can be predicted from another variable, e.g., the degree to which a patient's therapeutic response can be predicted from the pattern of binding between a set of interaction partners and a tumor sample taken from that patient. A variety of statistical methods may be used to measure correlation between two variables, e.g., without limitation the student t-test, the Fisher exact test, the Pearson correlation coefficient, the Spearman correlation coefficient, the Chi squared test, etc. Results are traditionally given as a measured correlation coefficient with a p-value that provides a measure of the likelihood that the correlation arose by chance. A correlation with a p-value that is less than 0.05 is generally considered to be statistically significant. Preferred correlations have p-values that are less than 0.01, especially less than 0.001.

Interaction partner—An "interaction partner" is an entity that physically associates with a tumor marker. For example and without limitation, an interaction partner may be an antibody or a fragment thereof that physically associates with a tumor marker. In general, an interaction partner is said to "associate specifically" with a tumor marker if it associates at a detectable level with the tumor marker and does not associate detectably with unrelated molecular entities (e.g., other tumor markers) under similar conditions. Specific association between a tumor marker and an interaction partner will typically be dependent upon the presence of a particular structural feature of the target tumor marker such as an antigenic determinant or epitope recognized by the interaction partner. Generally, if an interaction partner is specific for epitope A, the presence of a molecular entity (e.g., a protein) containing epitope A or the presence of free unlabeled A in a reaction containing both free labeled A and the interaction partner thereto, will reduce the amount of labeled A that binds to the interaction partner. In general, it is to be understood that specificity need not be absolute. For example, it is well known in the art that antibodies frequently cross-react with other epitopes in addition to the target epitope. Such cross-reactivity may be acceptable depending upon the application for which the interaction partner is to be used. Thus the degree of specificity of an interaction partner will depend on the context in which it is being used. In general, an interaction partner exhibits specificity for a particular tumor marker if it favors binding with that partner above binding with other potential partners, e.g., other tumor markers. One of ordinary skill in the art will be able to select interaction partners having a sufficient degree of specificity to perform appropriately in any given application (e.g., for detection of a target tumor marker, for therapeutic purposes, etc.). It is also to be understood that specificity may be evaluated in the context of additional factors such as the affinity of the interaction partner for the target tumor marker versus the affinity of the interaction partner for other potential partners, e.g., other tumor markers. If an interaction partner exhibits a high affinity for a target tumor marker and low affinity for non-target molecules, the interaction partner will likely be an acceptable reagent for diagnostic purposes even if it lacks specificity. It will be appreciated that once the specificity of an interaction partner is established in one or more contexts, it may be employed in other, preferably similar, contexts without necessarily re-evaluating its specificity.

Predictive panel—A "predictive panel" of interaction partners is a set of interaction partners whose collective pattern of binding or lack of binding to a tumor sample, when taken together, has sufficient correlation to classify the tumor sample as being from a patient who is likely (or not) to respond to a given therapeutic regimen.

Prognostic panel—A "prognostic panel" of interaction partners is a set of interaction partners whose collective pattern of binding or lack of binding to a tumor sample, when taken together, has sufficient correlation to classify the tumor sample as being from a patient who is likely to have a given outcome. Generally, "outcome" may include, but is not limited to, the average life expectancy of the patient, the likelihood that the patient will survive for a given amount of time (e.g., 6 months, 1 year, 5 years, etc.), the likelihood of recurrence, the likelihood that the patient will be disease-free for a specified prolonged period of time, or the likelihood that the patient will be cured of the disease.

Response—The "response" of a tumor or a cancer to therapy may represent any detectable change, for example at the molecular, cellular, organellar, or organismal level. For instance, tumor size, patient life expectancy, recurrence, or the length of time the patient survives, etc., are all responses. Responses can be measured in any of a variety of ways, including for example non-invasive measuring of tumor size (e.g., CT scan, image-enhanced visualization, etc.), invasive measuring of tumor size (e.g., residual tumor resection, etc.), surrogate marker measurement (e.g., serum PSA, etc.), clinical course variance (e.g., measurement of patient quality of life, time to relapse, survival time, etc.).

Small molecule—A "small molecule" is a non-polymeric molecule. A small molecule can be synthesized in a laboratory (e.g., by combinatorial synthesis) or found in nature (e.g., a natural product). A small molecule is typically characterized in that it contains several carbon-carbon bonds and has a molecular weight of less than about 1500 Da, although this characterization is not intended to be limiting for the purposes of the present invention.

Tumor markers—"Tumor markers" or "markers" are molecular entities that are detectable in tumor samples. Generally, tumor markers will be proteins that are present within the tumor sample, e.g., within the cytoplasm or membranes of tumor cells and/or secreted from such cells. According to the present invention, individual tumor markers or sets of tumor markers that correlate with tumor class or subclass are identified. Thus, subsequent tumor samples may be classified or subclassified based on the presence of these sets of tumor markers.

Tumor sample—As used herein the term "tumor sample" is taken broadly to include cell or tissue samples removed from a tumor, cells (or their progeny) derived from a tumor that may be located elsewhere in the body (e.g., cells in the bloodstream or at a site of metastasis), or any material derived by processing such a sample. Derived tumor samples may include, for example, nucleic acids or proteins extracted from the sample.

Detailed Description of Certain Preferred Embodiments of the Invention

As noted above, the present invention provides techniques and reagents for the classification and subclassification, of patients with HER2+ breast tumors. Such classification (or subclassification) has many beneficial applications. For example, a particular tumor class or subclass may correlate with prognosis and/or susceptibility to a particular therapeutic regimen. As such, the classification or subclassification may be used as the basis for a prognostic or predictive kit and may also be used as the basis for identifying previously unappreciated therapies. Therapies that are effective against only a particular class or subclass of tumor may have been lost in studies whose data were not stratified by subclass; the present invention allows such data to be re-stratified, and allows additional studies to be performed, so that class- or subclass-specific therapies may be identified and/or implemented. Alternatively or additionally, the present invention allows identification and/or implementation of therapies that are targeted to genes identified as class- or subclass-specific.

Classification and Subclassification of Tumors

In general, according to the present invention, HER2+ breast tumors are classified or subclassified on the basis of one or more tumor markers whose presence is correlated with a particular class or subclass. In preferred embodiments, the tumor markers are detected via their physical association with an interaction partner. Included in the present invention are kits comprising individual interaction partners or sets of interaction partners that together can be used to identify or classify a particular HER2+ breast tumor sample; such sets are generally referred to as "classification panels".

The present invention provides systems of identifying classification panels. In general, tumor samples are contacted with individual interaction partners, and binding between the interaction partners and their cognate tumor markers is detected. For example, panels of interaction partners that identify a particular class or subclass of HER2+ breast tumors may be defined by contacting individual interaction partners with a variety of different tumor samples (e.g., from different patients suffering from HER2+ breast cancer). Individual interaction partners may be selected for use a predictive markers or inclusion in the ultimate classification panel based on their binding to only a subset of the tumor samples. Those of ordinary skill in the art, however, will appreciate that all that is required for an interaction partner or a collection thereof to operate effectively as a classification panel is that the binding characteristic(s) of the interaction partner(s) alone or together are sufficient to classify a particular tumor sample.

The inventive process of identifying useful panels of interaction partners as described herein may itself result in the identification of new tumor classes or subclasses. That is, through the process of analyzing interaction partner binding patterns, investigators will often discover new tumor classes or subclasses to which sets of interaction partners bind. Thus, the processes (a) of defining classification panels of interaction partners for given tumor classes or subclasses; and (b) identifying new tumor classes or subclasses may well be experimentally interrelated. In general, the greater the number of tumor samples tested, the greater the likelihood that new classes or subclasses will be defined.

Often, when identifying sets of interaction partners that can act as a classification (or subclassification) panel, it will be desirable to obtain the largest set of tumor samples possible, and also to collect the largest amount of information possible about the individual samples. For example, the age of the patient, the staging of the tumor (e.g., according to the TNM system), any microscopic or submicroscopic characteristics of the tumor that may have been determined, may be recorded. Those of ordinary skill in the art will appreciate that the more information that is known about a tumor sample, the more aspects of that sample are available for correlation with interaction partner binding.

The systems of the present invention have particular utility in classifying or subclassifying tumor samples that are not otherwise distinguishable from one another. Thus, in some embodiments, it will be desirable to analyze the largest collection of tumor samples that are most similar to one another.

When obtaining tumor samples for testing according to the present invention, it is generally preferred that the samples represent or reflect characteristics of a population of patients or samples. It may also be useful to handle and process the samples under conditions and according to techniques common to clinical laboratories. Although the present invention is not intended to be limited to the strategies used for processing tumor samples, we note that, in the field of pathology, it is often common to fix samples in buffered formalin, and then to dehydrate them by immersion in increasing concentrations of ethanol followed by xylene. Samples are then embedded into paraffin, which is then molded into a "paraffin block" that is a standard intermediate in histologic processing of tissue samples. The present inventors have found that many useful interaction partners display comparable binding regardless of the method of preparation of tumor samples; those of ordinary skill in the art can readily adjust observations to account for differences in preparation procedure.

In preferred embodiments of the invention, large numbers of tissue samples are analyzed simultaneously. In some embodiments, a tissue array is prepared. Tissue arrays may be constructed according to a variety of techniques. According to one procedure, a commercially-available mechanical device (e.g., the manual tissue arrayer MTA1 from Beecher Instruments of Sun Prairie, Wis.) is used to remove an 0.6-micron-diameter, full thickness "core" from a paraffin block (the donor block) prepared from each patient, and to insert the core into a separate paraffin block (the recipient block) in a designated location on a grid. In preferred embodiments, cores from as many as about 400 patients can be inserted into a single recipient block; preferably, core-to-core spacing is approximately 1 mm. The resulting tissue array may be processed into thin sections for staining with interaction partners according to standard methods applicable to paraffin embedded material. Depending upon the thickness of the donor blocks, as well as the dimensions of the clinical material, a single tissue array can yield about 50-150 slides containing >75% relevant tumor material for assessment with interaction partners. Construction of two or more parallel tissue arrays of cores from the same cohort of patient samples can provide relevant tumor material from the same set of patients in duplicate or more. Of course, in some cases, additional samples will be present in one array and not another.

The present inventors have found that it is often desirable to evaluate some aspects of the binding characteristics of potential interaction partners before or while assessing the desirability of including them in an interaction panel. For example, the inventors have found that it is often desirable to perform a titration study in which different concentrations of the interaction partner are contacted with a diverse set of tissue samples derived from a variety of different tissues (e.g., normal and/or tumor) in order to identify a concentration or titer at which differential binding is observed. This titer is referred to herein as a "discriminating titer". Such differential staining may be observed between different tissue samples and/or between different cell types within a given tissue sample.

In general, any tissue sample may be used for this purpose (e.g., samples obtained from the epididymis, esophagus, gall bladder, kidneys, liver, lungs, lymph nodes, muscles, ovaries, pancreas, parathyroid glands, placenta, prostate, saliva, skin, spleen, stomach, testis, thymus, thyroid, tonsils, uterus, etc.). For such titration studies, greater diversity among samples is often preferred. Without intending to limit the present invention, the inventors observe that useful titers for particular interaction partners can typically be defined in a study of approximately 40-70 different tissue samples from about 20-40 different tissues.

Binding studies (for titration, for assessment of inclusion in a panel, or during use of a panel) may be performed in any format that allows specific interaction to be detected. Where large numbers of samples are to be handled, it may be desirable to utilize arrayed and/or automated formats. Particularly preferred formats include tissue arrays as discussed above. The staining of large numbers of samples derived from a variety of tumors in a tissue array format allows excellent comparative assessment of differential staining between or among samples under identical conditions. According to the present invention, staining patterns that identify at least about 10% of samples as binding with a particular interaction partner, or at least about 20, 30, 40, 50% or more of samples, are likely to represent "real" differential staining patterns (i.e., real variations in binding with interaction partner and not experimental variations, for example, due to sample processing or day to day variation in staining techniques).

Any available technique may be used to detect binding between an interaction partner and a tumor sample. One powerful and commonly used technique is to have a detectable label associated (directly or indirectly) with the interaction partner. For example, commonly-used labels that often are associated with antibodies used in binding studies include fluorochromes, enzymes, gold, iodine, etc. Tissue staining by bound interaction partners is then assessed, preferably by a trained pathologist or cytotechnologist. For example, a scoring system may be utilized to designate whether the interaction partner does or does not bind to (e.g., stain) the sample, whether it stains the sample strongly or weakly and/or whether useful information could not be obtained (e.g., because the sample was lost, there was no tumor in the sample or the result was otherwise ambiguous). Those of ordinary skill in the art will recognize that the precise characteristics of the scoring system are not critical to the invention. For example, staining may be assessed qualitatively or quantitatively; more or less subtle gradations of staining may be defined; etc.

Whatever the format, and whatever the detection strategy, identification of a discriminating titer can simplify binding studies to assess the desirability of using an interaction partner and including it in a panel. In such studies, the interaction partner is contacted with a plurality of different tumor samples that preferably have at least one common trait (e.g., tissue of origin), and often have multiple common traits (e.g., tissue of origin, stage, microscopic characteristics, etc.). In some cases, it will be desirable to select a group of samples with at least one common trait and at least one different trait, so that a panel of interaction partners is defined that distinguishes the different trait. In other cases, it will be desirable to select a group of samples with no detectable different traits, so that a panel of interaction partners is defined that distinguishes among previously indistinguishable samples. Those of ordinary skill in the art will understand, however, that the present invention often will allow both of these goals to be accomplished even in studies of sample collections with varying degrees of similarity and difference.

The examples describe the identification of HTF9C as a suitable classification marker. Thus, in certain embodiments, the present invention provides a method comprising steps of: obtaining a tumor sample from a patient having an HER2+ breast tumor; contacting the tumor sample with a first interaction partner directed to the HTF9C marker; and classifying the HER2+ breast tumor based upon binding of the first interaction partner to the tumor sample.

These methods may further comprise steps of providing positive and/or negative control samples and contacting the positive and/or negative control samples with a first interaction partner directed to the HTF9C marker. According to such embodiments, the step of classifying the HER2+ tumor may comprise a step of comparing the binding of the first interaction partner to the tumor sample with the binding of the first interaction partner to the positive and/or negative control samples. In one set of embodiments, the first interaction partner is an antibody, e.g., without limitation a monoclonal antibody.

As discussed above, it will be appreciated that the classification process may be extended by further contacting the tumor sample with interaction partners for one or more additional markers that stain HER2+ tumors differentially (e.g., the estrogen and progesterone receptors).

Assessing Prognosis or Therapeutic Regimen

The present invention further provides systems for identifying interaction partners and panels of interaction partners whose binding correlates with factors beyond HER2+ breast tumor class or subclass, such as likelihood of a particular favorable or unfavorable outcome, susceptibility (or lack thereof) to a particular therapeutic regimen, etc.

As mentioned in the background, current approaches to assigning prognostic probabilities and/or selecting appropriate therapeutic regimens for particular tumors generally utilize the tumor-node-metastasis (TNM) system. This system uses the size of the tumor, the presence or absence of tumor in regional lymph nodes and the presence or absence of distant metastases, to assign a stage to the tumor. The assigned stage is used as a basis for selection of appropriate therapy and for prognostic purposes.

The present invention provides new methods and systems for evaluating tumor prognosis and/or recommended therapeutic approaches. In particular, the present invention provides interaction partners (and systems for identifying other interaction partners and panels of interaction partners) whose binding correlates with HER2+ breast tumor prognosis or therapeutic outcome.

For example, interaction partners whose binding correlates with prognosis can be identified by evaluating their binding to a collection of HER2+ breast tumor samples for which prognosis is known or knowable. That is, the strategies of the invention may be employed either to identify collections of interaction partners whose binding correlates with a known outcome, or may be employed to identify a differential staining pattern that is then correlated with outcome (which outcome may either be known in advance or determined over time).

In general, it is preferred that inventive binding analyses be performed on human tumor samples. However, it is not necessary that the human tumors grow in a human host. Particularly for studies in which long-term outcome data are of interest (especially prognostic or predictive studies), it can be particularly useful to analyze samples grown in vitro (e.g., cell lines) or, more preferably, in a non-human host (e.g., a rodent, a dog, a sheep, a pig, or other animal). For instance, Example 5 provides a description of an assay in which inventive techniques employing human tumor cells growing in a non-human host are employed to define and/or utilize a panel of interaction partners whose binding to tumor samples correlates with prognosis and/or responsiveness to therapy.

It will often be desirable, when identifying interaction partners whose binding correlates with prognosis, to collect information about treatment regimens that may have been applied to the tumor whose sample is being assessed, in order to control for effects attributable to tumor therapy. Prognostic panel binding may correlate with outcome independent of treatment (Hayes et al., *J. Mamm. Gland Bio. Neo.* 6:375, 2001). Many prognostic markers, however, have both prognostic and predictive character (e.g., HER2 status). Many of the individual interaction partners that comprise a prognostic panel may likewise have predictive capability and/or be members of a predictive panel. This applies to the HTF9C marker identified in the examples.

Those of ordinary skill in the art will appreciate that prognostic panels (or individual interaction partners) have greater clinical utility if their binding/lack thereof correlates with positive/negative outcomes that are well separated statistically.

The inventive strategies may also be applied to the identification of predictive panels of interaction partners (i.e., panels whose binding correlates with susceptibility to a particular therapy). As noted above, some prognostic markers or panels may also have predictive capabilities.

Interaction partners to be included in predictive panels are identified in binding studies performed on HER2+ breast tumor samples that do or do not respond to a particular therapy. As with the prognostic panels, predictive panels may be assembled based on tests of tumor samples whose responsiveness is already known, or on samples whose responsiveness is not known in advance. As with the prognostic studies discussed above, the source of the tumor samples is not essential and can include, for example, tumor cell lines whose responsiveness to particular chemical agents has been determined, tumor samples from animal models in which tumors have been artificially introduced and therapeutic responsiveness has been determined and/or samples from naturally-occurring (human or other animal) tumors for which outcome data (e.g., time of survival, responsiveness to therapy, etc.) are available. Individual interaction partners and panels of interaction partners whose binding to tumor samples correlates with any prognostic or therapeutic trend can be defined and utilized as described herein.

Once correlations between interaction partner binding and tumor behavior have been established, the defined prognostic or predictive interaction partners or panels can be used to evaluate and classify tumor samples from patients and can be relied upon, for example to guide selection of an effective therapeutic regimen. As with the tumor classification studies described above, the process of identifying interaction partner panels whose binding correlates with outcome may itself identify particular outcomes not previously appreciated as distinct.

Those of ordinary skill in the art will appreciate that it is likely that, in at least some instances, tumor class or subclass identity will itself correlate with prognosis or responsiveness. In such circumstances, it is possible that the same interaction partner(s) can be used as tumor classifiers, prognosticators and predictors of therapeutic response.

The examples describe the identification of HTF9C as a suitable prognostic marker. Thus, in certain embodiments, the present invention provides a method comprising steps of: obtaining a tumor sample from a patient having an HER2+ breast tumor; contacting the tumor sample with a first interaction partner directed to the HTF9C marker; and assessing the patient's likely prognosis based upon binding of the first interaction partner to the tumor sample. These methods may further comprise steps of providing a positive control sample and contacting the positive control sample with a first interaction partner directed to the HTF9C marker. According to such embodiments, the step of assessing the patient's likely prognosis may comprise a step of comparing the binding of the first interaction partner to the tumor sample and the positive control sample. Certain methods may further involve using a negative control sample in the comparison process. In one set of embodiments, the first interaction partner is an antibody, e.g., without limitation a monoclonal antibody.

In one embodiment, this method (or any other method described herein) may include a step of confirming the HER2+ status of the breast tumor. It will be appreciated that this can be achieved by any method that can detect overexpression of HER2 (e.g., without limitation by immunohistochemistry or an in situ hybridization technique such as FISH).

In one embodiment, the method may include an additional step of contacting the tumor sample with a second interaction partner directed to another biomarker (e.g., the ER marker), wherein in the step of assessing, the patient's likely prognosis is assessed based upon binding of the first and second interaction partners to the tumor sample.

The results in the examples demonstrate that HER2+/HTF9C+ breast cancers are more likely to recur when treated with traditional cytotoxic therapy alone. More aggressive treatment in the adjuvant setting may therefore need to be considered for these patients, regardless of the other conventional risk factors. Conversely, for HER2+/HTF9C− tumors, one might consider less aggressive adjuvant therapy, particularly if there are any concerns over potential cardiac toxicity with Trastuzumab treatment. Given the dual concerns of current clinical practice where patients may be placed at risk of cardiac dysfunction without the benefit from Trastuzumab and other patients who may benefit from Trastuzumab but are currently not receiving it, a biomarker such as HTF9C showing risk in the absence of Trastuzumab administration will be useful to the clinician. Thus, in certain embodiments, depending on the patient's likely prognosis based on staining with HTF9C one may decide to withhold or proceed with a particular breast cancer therapeutic (e.g., treatment with Trastuzumab). For example, if a patient's likely prognosis is poor as predicted by HTF9C staining then more aggressive therapy may be recommended.

Tumor Elements Bound By Interaction Partners

The inventive strategies for identifying and utilizing interaction partners in classifying or analyzing tumor samples do not rely on any assumptions about the identity or characteristics of the tumor components bound by the interaction partners. So long as interaction partner binding correlates with some feature of interest, the inventive teachings apply. In many if not most, cases, however, it is expected that binding will be with a protein expressed by tumor cells, e.g., HTF9C or ER.

In some preferred embodiments of the invention, interaction partners bind to tumor markers that (a) are differentially expressed in tumor cells; (b) are members of protein families whose activities contribute to relevant biological events (e.g., gene families that have been implicated in cancer such as oncogenes, tumor suppressor genes, and genes that regulate apoptosis; gene families that have been implicated in drug resistance; etc.); (c) are present on or in the plasma membrane of the tumor cells; and/or (d) are the products of degradation of tumor components, which degradation products might be detectable in patient serum.

In fact, according to the present invention, interaction partners for analysis and use in inventive panels may sometimes be identified by first identifying a tumor-associated protein of interest, and then finding a potential interaction partner that binds with the protein. Binding by this potential interaction partner to tumor samples may then be assessed and utilized as described herein.

Work by the present inventors, as well as by others, has already demonstrated that studies of gene expression patterns in large tumor cohorts can identify novel tumor classes (see, for example, Perou et al., *Nature* 406:747, 2000; Sorlie et al., *Proc Natl Acad. Sci. USA* 98:10869, 2001; van't Veer et al., *Nature* 415:530, 2002; West et al., *Proc Natl. Acad. Sci. USA* 98:11462, 2001; Hedenfalk et al., *N. Engl. J. Med.* 344:539, 2001; Gruvberger et al., *Cancer Res.* 61:5979, 2001; MacDonald et al., *Nature Genet.* 29:143, 2001; Pomeroy et al., *Nature* 415:436, 2002; Jazaeri et al., *J. Natl Cancer Inst* 94:990, 2002; Welsh et al., *Proc. Natl. Acad. Sci. USA* 98:1176, 2001; Wang et al., *Gene* 229:101, 1999; Beer et al., *Nature Med.* 8:816, 2002; Garber et al., *Proc Natl Acad Sci USA* 98:13784, 2001; Bhattacharjee et al., *Proc Natl Acad Sci USA* 98:13790, 2001; Zou et al., *Oncogene* 21:4855, 2002; Lin et al., *Oncogene* 21:4120, 2002; Alon et al., *Proc Natl Acad Sci USA* 96:6745, 1999; Takahashi et al., *Proc Natl Acad Sci USA* 98:9754, 2001; Singh et al., *Cancer Cell* 1:203, 2002; LaTulippe et al., *Cancer Res.* 62:4499, 2002; Welsh et al., *Cancer Res.* 61:5974, 2001; Dhanasekaran et al., *Nature* 412:822, 2001; Hippo et al., *Cancer Res.* 62:233, 2002; Yeoh et al., *Cancer Cell* 1:133, 2002; Hofmann et al., *Lancet* 359: 481, 2002; Ferrando et al., *Cancer Cell* 1:75, 2002; Shipp et al., *Nature Med* 8:68, 2002; Rosenwald et al., *N. Engl. J. Med.* 346:1937, 2002; and Alizadeh et al., *Nature* 403:503, 2000, each of which is incorporated herein by reference).

The gene sets described in these publications are suitable candidates for genes that encode tumor markers whose interaction partners are useful in tumor classification and subclassification according to the present invention. Of particular interest are gene sets differentially expressed in HER2+ breast tumors.

Furthermore, in general, given that differentially expressed genes are likely to be responsible for the different phenotypic characteristics of tumors, the present invention recognizes that such genes will often encode tumor markers for which a useful interaction partner, that discriminates among tumor classes or subclasses, can likely be prepared. A differentially expressed gene is a gene whose transcript abundance varies between different samples, e.g., between different tumor samples, between normal versus tumor samples, etc. In general, the amount by which the expression varies and the number of samples in which the expression varies by that amount will depend upon the number of samples and the particular characteristics of the samples. One skilled in the art will be able to determine, based on knowledge of the samples, what constitutes a significant degree of differential expression. Such genes can be identified by any of a variety of techniques including, for instance, in situ hybridization, Northern blot, nucleic acid amplification techniques (e.g., PCR, quantitative PCR, the ligase chain reaction, etc.), and, most commonly, microarray analysis.

While these overexpressed genes represent potential candidates for classifying tumors, the skilled person will recognize that without additional studies (e.g., those described in the examples), one cannot predict the prognostic or predictive power of these markers (e.g., see Hayes et al., *J. Natl. Cancer Inst.* 88:1456-1466, 1996).

Furthermore, those of ordinary skill in the art will readily appreciate, reading the present disclosure, that the inventive processes described herein of identifying and/or using interaction partners whose binding (or lack thereof) correlates with an interesting tumor feature (e.g., tumor type or subtype, patient outcome, responsiveness of tumor or patient to therapy, etc.) inherently identifies both interaction partners of interest and the tumor markers to which they bind. Thus, one important aspect of the present invention is the identification of tumor markers whose ability (or lack thereof) to associate with an interaction partner correlates with a tumor characteristic of interest. Such tumor markers are useful as targets for identification of new therapeutic reagents, as well as of additional interaction partners useful in the practice of the present invention. Thus, it is to be understood that discussions of interaction partners presented herein are typically not limited to a particular interaction partner compound or entity, but may be generalized to include any compound or entity that binds to the relevant tumor marker(s) with requisite specificity and affinity.

Preparation of Interaction Partners

In general, interaction partners are entities that physically associate with selected tumor markers. Thus, any entity that binds detectably to a tumor marker may be utilized as an interaction partner in accordance with the present invention, so long as it binds with an appropriate combination of affinity and specificity.

Particularly preferred interaction partners are antibodies, or fragments (e.g., F(ab) fragments, F(ab')$_2$ fragments, Fv fragments, or sFv fragments, etc.; see, for example, Inbar et al., *Proc. Nat. Acad. Sci. USA* 69:2659, 1972; Hochman et al., *Biochem.* 15:2706, 1976; and Ehrlich et al., *Biochem.* 19:4091, 1980; Huston et al., *Proc. Nat. Acad. Sci. USA* 85:5879, 1998; U.S. Pat. Nos. 5,091,513 and 5,132,405 to Huston et al.; and U.S. Pat. No. 4,946,778 to Ladner et al., each of which is incorporated herein by reference). In certain embodiments, interaction partners may be selected from libraries of mutant antibodies (or fragments thereof). For example, collections of antibodies that each include different point mutations may be screened for their association with a tumor marker of interest. Yet further, chimeric antibodies may be used as interaction partners, e.g., "humanized" or "veneered" antibodies as described in greater detail below.

It is to be understood that the present invention is not limited to using antibodies or antibody fragments as interaction partners of inventive tumor markers. In particular, the present invention also encompasses the use of synthetic interaction partners that mimic the functions of antibodies. Several approaches to designing and/or identifying antibody mimics have been proposed and demonstrated (e.g., see the reviews by Hsieh-Wilson et al., *Acc. Chem. Res.* 29:164, 2000 and Peczuh and Hamilton, *Chem. Rev.* 100:2479, 2000). For example, small molecules that bind protein surfaces in a fashion similar to that of natural proteins have been identified by screening synthetic libraries of small molecules or natural product isolates (e.g., see Gallop et al., *J. Med. Chem.* 37:1233, 1994; Gordon et al., *J. Med. Chem.* 37:1385, 1994; DeWitt et al., *Proc. Natl. Acad. Sci. U.S.A.* 90:6909, 1993; Bunin et al., *Proc. Natl. Acad. Sci. U.S.A.* 91:4708, 1994; Virgilio and Ellman, *J. Am. Chem. Soc.* 116:11580, 1994; Wang et al., *J. Med. Chem.* 38:2995, 1995; and Kick and Ellman, *J. Med. Chem.* 38:1427, 1995). Similarly, combinatorial approaches have been successfully applied to screen libraries of peptides and polypeptides for their ability to bind a range of proteins (e.g., see Cull et al., *Proc. Natl. Acad. Sci. U.S.A.* 89:1865, 1992; Mattheakis et al., *Proc. Natl. Acad. Sci. U.S.A.* 91:9022, 1994; Scott and Smith, *Science* 249:386, 1990; Devlin et al., *Science* 249:404, 1990; Corey et al., *Gene* 128:129, 1993; Bray et al., *Tetrahedron Lett.* 31:5811, 1990; Fodor et al., *Science* 251:767, 1991; Houghten et al., *Nature* 354:84, 1991; Lam et al., *Nature* 354:82, 1991; Blake and Litzi-Davis, *Bioconjugate Chem.* 3:510, 1992; Needels et al., *Proc. Natl. Acad. Sci. U.S.A.* 90:10700, 1993; and Ohlmeyer et al., *Proc. Natl. Acad. Sci. U.S.A.* 90:10922, 1993). Similar approaches have also been used to study carbohydrate-protein interactions (e.g., see Oldenburg et al., *Proc. Natl. Acad. Sci. U.S.A.* 89:5393, 1992) and polynucleotide-protein interactions (e.g., see Ellington and Szostak, *Nature* 346:818, 1990 and Tuerk and Gold, *Science* 249:505, 1990). These approaches have also been extended to study interactions between proteins and unnatural biopolymers such as oligocarbamates, oligoureas, oligosulfones, etc. (e.g., see Zuckermann et al., *J. Am. Chem. Soc.* 114:10646, 1992; Simon et al., *Proc. Natl. Acad. Sci. U.S.A.* 89:9367, 1992; Zuckermann et al., *J. Med. Chem.* 37:2678, 1994; Burgess et al., *Angew. Chem., Int. Ed. Engl.* 34:907, 1995; and Cho et al., *Science* 261:1303, 1993). Yet further, alternative protein scaffolds that are loosely based around the basic fold of antibody molecules have been suggested and may be used in the preparation of inventive interaction partners (e.g., see Ku and Schultz *Proc. Natl. Acad. Sci. U.S.A.* 92:6552, 1995). Antibody mimics comprising a scaffold of a small molecule such as 3-aminomethylbenzoic acid and a substituent consisting of a single peptide loop have also been constructed. The peptide loop performs the binding function in these mimics (e.g., see Smythe et al., *J. Am. Chem. Soc.* 116:2725, 1994). A synthetic antibody mimic comprising multiple peptide loops built around a calixarene unit has also been described (e.g., see U.S. Pat. No. 5,770,380 to Hamilton et al.).

Detecting Association of Interaction Partners and Tumor Markers

Any available strategy or system may be utilized to detect association between an interaction partner and its cognate tumor marker. In certain embodiments, association can be detected by adding a detectable label to the interaction partner. In other embodiments, association can be detected by using a labeled secondary interaction partner that associates specifically with the primary interaction partner, e.g., as is well known in the art of antigen/antibody detection. The detectable label may be directly detectable or indirectly detectable, e.g., through combined action with one or more additional members of a signal producing system. Examples of directly detectable labels include radioactive, paramagnetic, fluorescent, light scattering, absorptive and colorimetric labels. Examples of indirectly detectable include chemiluminescent labels, e.g., enzymes that are capable of converting a substrate to a chromogenic product such as alkaline phosphatase, horseradish peroxidase and the like.

Once a labeled interaction partner has bound a tumor marker, the complex may be visualized or detected in a variety of ways, with the particular manner of detection being chosen based on the particular detectable label, where representative detection means include, e.g., scintillation counting, autoradiography, measurement of paramagnetism, fluorescence measurement, light absorption measurement, measurement of light scattering and the like.

In general, association between an interaction partner and its cognate tumor marker may be assayed by contacting the interaction partner with a tumor sample that includes the marker. Depending upon the nature of the sample, appropriate methods include, but are not limited to, immunohistochemistry (IHC), radioimmunoassay, ELISA, immunoblotting and fluorescence activates cell sorting (FACS). In the case where the polypeptide is to be detected in a tissue sample, e.g., a biopsy sample, IHC is a particularly appropriate detection method. Techniques for obtaining tissue and cell samples and performing IHC and FACS are well known in the art.

As discussed above and in the Examples, the inventors have applied these techniques to tumor samples from HER2+ breast cancer patients. The invention also encompasses the recognition that tumor markers that are secreted from the cells in which they are produced may be present in serum, enabling their detection through a blood test rather than requiring a biopsy specimen. An interaction partner that binds to such tumor markers represents a particularly preferred embodiment of the invention.

In general, the results of such an assay can be presented in any of a variety of formats. The results can be presented in a qualitative fashion. For example, the test report may indicate only whether or not a particular tumor marker was detected, perhaps also with an indication of the limits of detection. Additionally the test report may indicate the subcellular location of binding, e.g., nuclear versus cytoplasmic and/or the relative levels of binding in these different subcellular locations. The results may be presented in a semi-quantitative fashion. For example, various ranges may be defined and the ranges may be assigned a score (e.g., 0 to 5) that provides a certain degree of quantitative information. Such a score may reflect various factors, e.g., the number of cells in which the tumor marker is detected, the intensity of the signal (which may indicate the level of expression of the tumor marker), etc. The results may be presented in a quantitative fashion, e.g., as a percentage of cells in which the tumor marker is detected, as a concentration, etc. As will be appreciated by one of ordinary skill in the art, the type of output provided by a test will vary depending upon the technical limitations of the test and the biological significance associated with detection of the tumor marker. For example, in the case of certain tumor markers a purely qualitative output (e.g., whether or not the tumor marker is detected at a certain detection level) provides significant information. In other cases a more quantitative output (e.g., a ratio of the level of expression of the tumor marker in two samples) is necessary.

Identification of Novel Therapies

Predictive interaction partners and panels are useful according to the present invention not only to classify tumor samples obtained from HER2+ breast cancer sufferers with respect to their likely responsiveness to known therapies, but also to identify potential new therapies or therapeutic agents that could be useful in the treatment of cancer.

For example, as noted above, the process of identifying or using interaction partners according to the present invention simultaneously identifies and/or characterizes tumor markers in or on the tumor cells that correlate with one or more selected tumor characteristics (e.g., tumor type or subtype, patient prognosis, and/or responsiveness of tumor or patient to therapy). Such tumor markers are attractive candidates for identification of new therapeutic agents (e.g., via screens to detect compounds or entities that bind to the tumor markers, preferably with at least a specified affinity and/or specificity, and/or via screens to detect compounds or entities that modulate (i.e., increase or decrease) expression, localization, modification, or activity of the tumor markers. Thus, in one embodiment the present invention provides methods comprising steps of contacting a test compound with a cell expressing the HTF9C marker (e.g., individual engineered cells or in the context of a tissue, etc.); and determining whether the test compound modulates the expression, localization, modification, or activity of the HTF9C marker. In many instances, interaction partners themselves may prove to be useful therapeutics.

Thus the present invention provides interaction partners that are themselves useful therapeutic agents. For example, binding by an antibody raised against HTF9C to cells in a HER2+ breast tumor might inhibit growth of those cells. Alternatively or additionally, interaction partners defined or prepared according to the present invention could be used to deliver a therapeutic agent to a cancer cell. In particular, interaction partners (e.g., an antibody raised against HTF9C) may be coupled to one or more therapeutic agents. Suitable agents in this regard include radionuclides and drugs. Preferred radionuclides include $^{90}$Y, $^{123}$I, $^{125}$I, $^{131}$I, $^{186}$Re, $^{188}$Re, $^{211}$At and $^{212}$Bi. Preferred drugs include chlorambucil, ifosphamide, mechlorethamine, cyclophosphamide, carboplatin, cisplatin, procarbazine, decarbazine, carmustine, cytarabine, hydroxyurea, mercaptopurine, methotrexate, thioguanine, 5-fluorouracil, actinomycin D, bleomycin, daunorubicin, doxorubicin, etoposide, vinblastine, vincristine, L-asparginase, adrenocorticosteroids, canciclovir triphosphate, adenine arabinonucleoside triphosphate, 5-aziridinyl-4-hydroxy-lamino-2-nitrobenzamide, acrolein, phosphoramide mustard, 6-methylpurine, etoposide, methotrexate, benzoic acid mustard, cyanide and nitrogen mustard.

According to such embodiments, the therapeutic agent may be coupled with an interaction partner by direct or indirect covalent or non-covalent interactions. A direct interaction between a therapeutic agent and an interaction partner is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other. Indirect interactions might involve a linker group that is itself associated with both the therapeutic agent and the interaction partner. A linker group can function as a spacer to distance an interaction partner from an agent in order to avoid interference with association capabilities. A linker group can also serve to increase the chemical reactivity of a substituent on an agent or an interaction partner and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfydryl groups or oxidized carbohydrate residues. There are numerous references describing such methodology, e.g., U.S. Pat. No. 4,671,958, to Rodwell et al. It will further be appreciated that a therapeutic agent and an interaction partner may be coupled via non-covalent interactions, e.g., ligand/receptor type interactions. Any ligand/receptor pair with a sufficient stability and specificity to operate in the context of the invention may be employed to couple a therapeutic agent and an interaction partner. To give but an example, a therapeutic agent may be covalently linked with biotin and an interaction partner with avidin. The strong non-covalent binding of biotin to avidin would then allow for coupling of the therapeutic agent and the interaction partner. Typical ligand/receptor pairs include protein/co-factor and enzyme/substrate pairs. Besides the commonly used biotin/avidin pair, these include without limitation, biotin/streptavidin, digoxigenin/anti-digoxigenin, FK506/FK506-binding protein (FKBP), rapamycin/FKBP, cyclophilin/cyclosporin and glutathione/glutathione transferase pairs. Other suitable ligand/receptor pairs would be recognized by those skilled in the art, e.g., monoclonal antibodies paired with a epitope tag such as, without limitation, glutathione-S-transferase (GST), c-myc, FLAG® and maltose binding protein (MBP) and further those described in Kessler pp. 105-152 of *Advances in Mutagenesis*" Ed. by Kessler, Springer-Verlag, 1990; *"Affinity Chromatography: Methods and Protocols (Methods in Molecular Biology)*" Ed. by Pascal Baillon, Humana Press, 2000; and *"Immobilized Affinity Ligand Techniques"* by Hermanson et al., Academic Press, 1992.

Where a therapeutic agent is more potent when free from the interaction partner, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710 to Spitler), by irradiation of a photolabile bond (e.g., U.S. Pat. No. 4,625,014 to Senter et al.), by hydrolysis of derivatized amino acid side chains (e.g., U.S. Pat. No. 4,638,045 to Kohn et al.), by serum complement-mediated hydrolysis (e.g., U.S. Pat. No. 4,671,958 to Rodwell et al.) and by acid-catalyzed hydrolysis (e.g., U.S. Pat. No. 4,569,789 to Blättler et al.).

In certain embodiments, it may be desirable to couple more than one therapeutic agent to an interaction partner. In one embodiment, multiple molecules of an agent are coupled to one interaction partner molecule. In another embodiment, more than one type of therapeutic agent may be coupled to one interaction partner molecule. Regardless of the particular embodiment, preparations with more than one agent may be prepared in a variety of ways. For example, more than one agent may be coupled directly to an interaction partner molecule, or linkers that provide multiple sites for attachment can be used.

Alternatively, a carrier can be used. A carrier may bear the agents in a variety of ways, including covalent bonding either directly or via a linker group. Suitable carriers include proteins such as albumins (e.g., U.S. Pat. No. 4,507,234 to Kato et al.), peptides, and polysaccharides such as aminodextran (e.g., U.S. Pat. No. 4,699,784 to Shih et al.). A carrier may also bear an agent by non-covalent bonding or by encapsulation, such as within a liposome vesicle (e.g., U.S. Pat. No. 4,429,008 to Martin et al. and U.S. Pat. No. 4,873,088 to Mayhew et al.). Carriers specific for radionuclide agents include radiohalogenated small molecules and chelating compounds. For example, U.S. Pat. No. 4,735,792 to Srivastava discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562 to Davison et al. discloses representative chelating compounds and their synthesis.

When interaction partners are themselves therapeutics, it will be understood that, in many cases, any interaction partner that binds with the same tumor marker may be so used.

In one preferred embodiment of the invention, the therapeutic agents (whether interaction partners or otherwise) are antibodies, e.g., an antibody against the HTF9C marker. As is well known in the art, when using an antibody or fragment thereof for therapeutic purposes it may prove advantageous to use a "humanized" or "veneered" version of an antibody of interest to reduce any potential immunogenic reaction. In general, "humanized" or "veneered" antibody molecules and fragments thereof minimize unwanted immunological responses toward antihuman antibody molecules which can limit the duration and effectiveness of therapeutic applications of those moieties in human recipients.

A number of "humanized" antibody molecules comprising an antigen binding portion derived from a non-human immunoglobulin have been described in the art, including chimeric antibodies having rodent variable regions and their associated complementarity-determining regions (CDRs) fused to human constant domains (e.g., see Winter et al., *Nature* 349: 293, 1991; Lobuglio et al., *Proc. Nat. Acad. Sci. USA* 86:4220, 1989; Shaw et al., *J. Immunol.* 138:4534, 1987; and Brown et al., *Cancer Res.* 47:3577, 1987), rodent CDRs grafted into a human supporting framework region (FR) prior to fusion with an appropriate human antibody constant domain (e.g., see Riechmann et al., *Nature* 332:323, 1988; Verhoeyen et al., *Science* 239:1534, 1988; and Jones et al. *Nature* 321:522, 1986) and rodent CDRs supported by recombinantly veneered rodent FRs (e.g., see European Patent Publication No. 519,596, published Dec. 23, 1992). It is to be understood that the invention also encompasses "fully human" antibodies produced using the XenoMouse™ technology (AbGenix Corp., Fremont, Calif.) according to the techniques described in U.S. Pat. No. 6,075,181.

Yet further, so-called "veneered" antibodies may be used that include "veneered FRs". The process of veneering involves selectively replacing FR residues from, e.g., a murine heavy or light chain variable region, with human FR residues in order to provide a xenogeneic molecule comprising an antigen binding portion which retains substantially all of the native FR polypeptide folding structure. Veneering techniques are based on the understanding that the antigen binding characteristics of an antigen binding portion are determined primarily by the structure and relative disposition of the heavy and light chain CDR sets within the antigen-association surface (e.g., see Davies et al., *Ann. Rev. Biochem.* 59:439, 1990). Thus, antigen association specificity can be preserved in a humanized antibody only wherein the CDR structures, their interaction with each other and their interaction with the rest of the variable region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

Preferably, interaction partners suitable for use as therapeutics (or therapeutic agent carriers) exhibit high specificity for the target tumor marker (e.g., HTF9C) and low background binding to other tumor markers. In certain embodiments, monoclonal antibodies are preferred for therapeutic purposes.

Kits

A useful interaction partner or panels of interaction partners may be prepared and packaged together in kits for use in classifying, diagnosing, or otherwise characterizing HER2+ breast tumor samples, or for inhibiting tumor cell growth or otherwise treating HER2+ breast cancer.

Any available technique may be utilized in the preparation of individual interaction partners for inclusion in kits. For example, protein or polypeptide interaction partners may be produced by cells (e.g., recombinantly or otherwise), may be chemically synthesized, or may be otherwise generated in vitro (e.g., via in vitro transcription and/or translation). Non-protein or polypeptide interaction partners (e.g., small molecules, etc.) may be synthesized, may be isolated from within or around cells that produce them, or may be otherwise generated.

When antibodies are used as interaction partners, these may be prepared by any of a variety of techniques known to those of ordinary skill in the art (e.g., see Harlow and Lane, *Antibodies: A Laboratory Manual*, Cold Spring Harbor Laboratory, 1988). For example, antibodies can be produced by cell culture techniques, including the generation of monoclonal antibodies, or via transfection of antibody genes into suitable bacterial or mammalian cell hosts, in order to allow for the production of recombinant antibodies. In one technique, an "immunogen" comprising an antigenic portion of a tumor marker of interest (or the tumor marker itself) is initially injected into any of a wide variety of mammals (e.g., mice, rats, rabbits, sheep or goats). In this step, a tumor marker (or an antigenic portion thereof) may serve as the immunogen without modification. Alternatively, particularly for relatively short tumor markers, a superior immune response may be elicited if the tumor marker is joined to a carrier protein, such as bovine serum albumin or keyhole limpet hemocyanin (KLH). The immunogen is injected into the animal host, preferably according to a predetermined schedule incorporating one or more booster immunizations and the animals are bled periodically. Polyclonal antibodies specific for the tumor marker may then be purified from such antisera by, for example, affinity chromatography using the tumor marker (or an antigenic portion thereof) coupled to a suitable solid support. An exemplary method is described in Example 7.

If desired for diagnostic or therapeutic kits, monoclonal antibodies specific for a tumor marker of interest may be prepared, for example, using the technique of Kohler and Milstein, *Eur. J. Immunol.* 6:511, 1976 and improvements thereto. Briefly, these methods involve the preparation of immortal cell lines capable of producing antibodies having the desired specificity (i.e., reactivity with the tumor marker of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the tumor marker. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation and extraction. The tumor marker of interest may be used in the purification process in, for example, an affinity chromatography step.

In addition to inventive interaction partners, preferred kits for use in accordance with the present invention may include, one or more reference samples (e.g., positive and negative controls), instructions for processing samples, performing the test, instructions for interpreting the results, buffers and/or other reagents necessary for performing the test. In certain embodiments the kit can comprise a panel of antibodies. For example, a kit might include antibodies directed to the HTF9C and HER2 markers. In some embodiments, a kit might include antibodies directed to the HTF9C and ER markers. In some embodiments, a kit might include antibodies directed to the HTF9C, HER2 and ER markers. In each case, a kit might also include positive and negative control samples.

Pharmaceutical Compositions

As mentioned above, the present invention provides new therapies and methods for identifying these. In certain embodiments, an interaction partner may be a useful therapeutic agent. Alternatively or additionally, interaction partners defined or prepared according to the present invention bind to tumor markers that serve as targets for therapeutic agents. Also, inventive interaction partners may be used to deliver a therapeutic agent to a cancer cell. For example, interaction partners provided in accordance with the present invention may be coupled to one or more therapeutic agents.

In addition, as mentioned above, to the extent that a particular interaction partner or panel of interaction partners correlates with responsiveness to a particular therapy because it detects changes that reflect inhibition (or inhibitability) of cancer cell growth, that panel could be used to evaluate therapeutic candidates (e.g., small molecule drugs) for their ability to induce the same or similar changes in different cells. In particular, binding by the panel could be assessed on cancer cells before and after exposure to candidate therapeutics; those candidates that induce expression of the tumor markers to which the interaction partner(s) binds are then identified.

The invention includes pharmaceutical compositions comprising these inventive therapeutic agents. In general, a pharmaceutical composition will include a therapeutic agent in addition to one or more inactive agents such as a sterile, biocompatible carrier including, but not limited to, sterile water, saline, buffered saline, or dextrose solution. The pharmaceutical compositions may be administered either alone or in combination with other therapeutic agents including other chemotherapeutic agents, hormones, vaccines and/or radiation therapy. By "in combination with", it is not intended to imply that the agents must be administered at the same time or formulated for delivery together, although these methods of delivery are within the scope of the invention. In general, each agent will be administered at a dose and on a time schedule determined for that agent. Additionally, the invention encompasses the delivery of the inventive pharmaceutical compositions in combination with agents that may improve their bioavailability, reduce or modify their metabolism, inhibit their excretion, or modify their distribution within the body. The invention encompasses treating HER2+ breast cancer by administering the pharmaceutical compositions of the invention. Although the pharmaceutical compositions of the present invention can be used for treatment of any subject (e.g., any animal) in need thereof, they are most preferably used in the treatment of humans.

The pharmaceutical compositions of this invention can be administered to humans and other animals by a variety of routes including oral, intravenous, intramuscular, intra-arterial, subcutaneous, intraventricular, transdermal, rectal, intravaginal, intraperitoneal, topical (as by powders, ointments, or drops), bucal, or as an oral or nasal spray or aerosol. In general the most appropriate route of administration will depend upon a variety of factors including the nature of the agent (e.g., its stability in the environment of the gastrointestinal tract), the condition of the patient (e.g., whether the patient is able to tolerate oral administration), etc. At present the intravenous route is most commonly used to deliver therapeutic antibodies. However, the invention encompasses the delivery of the inventive pharmaceutical composition by any appropriate route taking into consideration likely advances in the sciences of drug delivery.

General considerations in the formulation and manufacture of pharmaceutical agents may be found, for example, in *Remington's Pharmaceutical Sciences*, 19$^{th}$ ed., Mack Publishing Co., Easton, Pa., 1995.

According to the methods of treatment of the present invention, HER2+ breast cancer is treated or prevented in a patient such as a human or other mammal by administering to the patient a therapeutically effective amount of a therapeutic agent of the invention, in such amounts and for such time as is necessary to achieve the desired result. By a "therapeutically effective amount" of a therapeutic agent of the invention is meant a sufficient amount of the therapeutic agent to treat (e.g., to ameliorate the symptoms of, delay progression of, prevent recurrence of, cure, etc.) cancer at a reasonable benefit/risk ratio, which involves a balancing of the efficacy and toxicity of the therapeutic agent. In general, therapeutic efficacy and toxicity may be determined by standard pharmacological procedures in cell cultures or with experimental animals, e.g., by calculating the $ED_{50}$ (the dose that is therapeutically effective in 50% of the treated subjects) and the $LD_{50}$ (the dose that is lethal to 50% of treated subjects). The $ED_{50}/LD_{50}$ represents the therapeutic index of the agent. Although in general therapeutic agents having a large therapeutic index are preferred, as is well known in the art, a smaller therapeutic index may be acceptable in the case of a serious disease, particularly in the absence of alternative therapeutic options. Ultimate selection of an appropriate range of doses for administration to humans is determined in the course of clinical trials.

It will be understood that the total daily usage of the therapeutic agents and compositions of the present invention for any given patient will be decided by the attending physician within the scope of sound medical judgment. The specific therapeutically effective dose level for any particular patient will depend upon a variety of factors including the disorder being treated and the severity of the disorder; the activity of the specific therapeutic agent employed; the specific composition employed; the age, body weight, general health and diet of the patient; the time of administration, route of administration and rate of excretion of the specific therapeutic agent employed; the duration of the treatment; drugs used in combination or coincidental with the specific therapeutic agent employed; and like factors well known in the medical arts.

The total daily dose of the therapeutic agents of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 0.1 µg to about 2000 mg of the therapeutic agent(s) of the invention per day in single or multiple doses.

EXEMPLIFICATION

Example 1

Raising Antibodies

This example describes a method that was employed to generate the majority of the antibodies that were used in these Examples. Similar methods may be used to generate an antibody that binds to any polypeptide of interest (e.g., to polypeptides that are or are derived from other tumor markers). In some cases, antibodies may be obtained from commercial sources (e.g., Chemicon, Dako, Oncogene Research Products, NeoMarkers, etc.) or other publicly available sources (e.g., Imperial Cancer Research Technology, etc.).

Materials and Solutions

Anisole (Cat. No. A4405, Sigma, St. Louis, Mo.)
2,2'-azino-di-(3-ethyl-benzothiazoline-sulfonic acid) (ABTS) (Cat. No. A6499, Molecular Probes, Eugene, Oreg.)
Activated maleimide Keyhole Limpet Hemocyanin (Cat. No. 77106, Pierce, Rockford, Ill.)
Keyhole Limpet Hemocyanin (Cat. No. 77600, Pierce, Rockford, Ill.)
Phosphoric Acid ($H_3PO_4$) (Cat. No. P6560, Sigma)
Glacial Acetic Acid (Cat No. BP1185-500, Fisher)
EDC (EDAC) (Cat No. 341006, Calbiochem)
25% Glutaraldehyde (Cat No. G-5882, Sigma)
Glycine (Cat No. G-8898, Sigma)
Biotin (Cat. No. B2643, Sigma)
Boric acid (Cat. No. B0252, Sigma)
Sepharose 4B (Cat. No. 17-0120-01, LKB/Pharmacia, Uppsala, Sweden)
Bovine Serum Albumin (LP) (Cat. No. 100 350, Boehringer Mannheim, Indianapolis, Ind.)
Cyanogen bromide (Cat. No. C6388, Sigma)
Dialysis tubing Spectra/Por Membrane MWCO: 6-8,000 (Cat. No. 132 665, Spectrum Industries, Laguna Hills, Calif.)
Dimethyl formamide (DMF) (Cat. No. 22705-6, Aldrich, Milwaukee, Wis.)
DIC (Cat. No. BP 592-500, Fisher)
Ethanedithiol (Cat. No. 39, 802-0, Aldrich)
Ether (Cat. No. TX 1275-3, EM Sciences)
Ethylenediaminetetraacetatic acid (EDTA) (Cat. No. BP 120-1, Fisher, Springfield, N.J.)
1-ethyl-3-(3' dimethylaminopropyl)-carbodiimide, HCL (EDC) (Cat. no. 341-006, Calbiochem, San Diego, Calif.)
Freund's Adjuvant, complete (Cat. No. M-0638-50B, Lee Laboratories, Grayson, Ga.)
Freund's Adjuvant, incomplete (Cat. No. M-0639-50B, Lee Laboratories)
Fritted chromatography columns (Column part No. 12131011; Frit Part No. 12131029, Varian Sample Preparation Products, Harbor City, Calif.)
Gelatin from Bovine Skin (Cat. No. G9382, Sigma)
Goat anti-rabbit IgG, biotinylated (Cat. No. A 0418, Sigma)
HOBt (Cat. No. 01-62-0008, Calbiochem)
Horseradish peroxidase (HRP) (Cat. No. 814 393, Boehringer Mannheim)
HRP-Streptavidin (Cat. No. S 5512, Sigma)
Hydrochloric Acid (Cat. No. 71445-500, Fisher)
Hydrogen Peroxide 30% w/w (Cat. No. H1009, Sigma)
Methanol (Cat. No. A412-20, Fisher)
Microtiter plates, 96 well (Cat. No. 2595, Corning-Costar, Pleasanton, Calif.)
N-α-Fmoc protected amino acids from Calbiochem. See '97-'98 Catalog pp. 1-45.
N-α-Fmoc protected amino acids attached to Wang Resin from Calbiochem. See '97-'98 Catalog pp. 161-164.
NMP (Cat. No. CAS 872-50-4, Burdick and Jackson, Muskegon, Mich.)
Peptide (Synthesized by Research Genetics. Details given below)
Piperidine (Cat. No. 80640, Fluka, available through Sigma)
Sodium Bicarbonate (Cat. No. BP328-1, Fisher)
Sodium Borate (Cat. No. B9876, Sigma)
Sodium Carbonate (Cat. No. BP357-1, Fisher)
Sodium Chloride (Cat. No. BP 358-10, Fisher)
Sodium Hydroxide (Cat. No. SS 255-1, Fisher)
Streptavidin (Cat. No. 1 520, Boehringer Mannheim)
Thioanisole (Cat. No. T-2765, Sigma)
Trifluoroacetic acid (Cat. No. TX 1275-3, EM Sciences)
Tween-20 (Cat. No. BP 337-500, Fisher)
Wetbox (Rectangular Servin' Saver™ Part No. 3862, Rubbermaid, Wooster, Ohio)
BBS—Borate Buffered Saline with EDTA dissolved in distilled water (pH 8.2 to 8.4 with HCl or NaOH), 25 mM Sodium borate (Borax), 100 mM Boric Acid, 75 mM NaCl and 5 mM EDTA.
0.1 N HCl in saline as follows: concentrated HCl (8.3 ml/0.917 liter distilled water) and 0.154 M NaCl
Glycine (pH 2.0 and pH 3.0) dissolved in distilled water and adjusted to the desired pH, 0.1 M glycine and 0.154 M NaCl.
5× Borate 1× Sodium Chloride dissolved in distilled water, 0.11 M NaCl, 60 mM Sodium Borate and 250 mM Boric Acid.
Substrate Buffer in distilled water adjusted to pH 4.0 with sodium hydroxide, 50 to 100 mM Citric Acid.
AA solution: HOBt is dissolved in NMP (8.8 grams HOBt to 1 liter NMP). Fmoc-N-a-amino at a concentration at 0.53 M.
DIC solution: 1 part DIC to 3 parts NMP.
Deprotecting solution: 1 part Piperidine to 3 parts DMF.
Reagent R: 2 parts anisole, 3 parts ethanedithiol, 5 parts thioanisole and 90 parts trifluoroacetic acid.

Equipment
MRX Plate Reader (Dynatech, Chantilly, Va.)
Hamilton Eclipse (Hamilton Instruments, Reno, Nev.)

Beckman TJ-6 Centrifuge (Model No. TJ-6, Beckman Instruments, Fullerton, Calif.)

Chart Recorder (Recorder 1 Part No. 18-1001-40, Pharmacia LKB Biotechnology)

UV Monitor (Uvicord SII Part No. 18-1004-50, Pharmacia LKB Biotechnology)

Amicon Stirred Cell Concentrator (Model 8400, Amicon, Beverly, Mass.)

30 kD MW cut-off filter (Cat. No. YM-30 Membranes Cat. No. 13742, Amicon)

Multi-channel Automated Pipettor (Cat. No. 4880, Corning Costar, Cambridge, Mass.)

pH Meter Corning 240 (Corning Science Products, Corning Glassworks, Corning, N.Y.)

ACT396 peptide synthesizer (Advanced ChemTech, Louisville, Ky.)

Vacuum dryer (Box from Labconco, Kansas City, Mo. and Pump from Alcatel, Laurel, Md.).

Lyophilizer (Unitop 600sl in tandem with Freezemobile 12, both from Virtis, Gardiner, N.Y.)

Peptide Selection

Peptides against which antibodies would be raised were selected from within the polypeptide sequence of interest using a program that uses the Hopp/Woods method (described in Hopp and Woods, *Mol. Immunol.* 20:483, 1983 and Hopp and Woods, *Proc. Nat. Acad. Sci. U.S.A.* 78:3824, 1981). The program uses a scanning window that identifies peptide sequences of 15-20 amino acids containing several putative antigenic epitopes as predicted by low solvent accessibility. This is in contrast to most implementations of the Hopp/Woods method, which identify single short (~6 amino acids) presumptive antigenic epitopes. Occasionally the predicted solvent accessibility was further assessed by PHD prediction of loop structures (described in Rost and Sander, *Proteins* 20:216, 1994). Preferred peptide sequences display minimal similarity with additional known human proteins. Similarity was determined by performing BLASTP alignments, using a wordsize of 2 (described in Altschul et al., *J. Mol. Biol.* 215:403, 1990). All alignments given an EXPECT value less than 1000 were examined and alignments with similarities of greater than 60% or more than four residues in an exact contiguous non-gapped alignment forced those peptides to be rejected. When it was desired to target regions of proteins exposed outside the cell membrane, extracellular regions of the protein of interest were determined from the literature or as defined by predicted transmembrane domains using a hidden Markov model (described in Krogh et al., *J. Mol. Biol.* 305:567, 2001). When the peptide sequence was in an extracellular domain, peptides were rejected if they contained N-linked glycosylation sites. As shown in Appendix A, one to three peptide sequences were selected for each polypeptide using this procedure.

Peptide Synthesis

The sequence of the desired peptide was provided to the peptide synthesizer. The C-terminal residue was determined and the appropriate Wang Resin was attached to the reaction vessel. The peptides were synthesized C-terminus to N-terminus by adding one amino acid at a time using a synthesis cycle. Which amino acid is added was controlled by the peptide synthesizer, which looks to the sequence of the peptide that was entered into its database. The synthesis steps were performed as follows:

Step 1—Resin Swelling: Added 2 ml DMF, incubated 30 minutes, drained DMF.

Step 2—Synthesis cycle (repeated over the length of the peptide)

2a—Deprotection: 1 ml deprotecting solution was added to the reaction vessel and incubated for 20 minutes.

2b—Wash Cycle

2c—Coupling: 750 ml of amino acid solution (changed as the sequence listed in the peptide synthesizer dictated) and 250 ml of DIC solution were added to the reaction vessel. The reaction vessel was incubated for thirty minutes and washed once. The coupling step was repeated once.

2d—Wash Cycle

Step 3—Final Deprotection: Steps 2a and 2b were performed one last time.

Resins were deswelled in methanol (rinsed twice in 5 ml methanol, incubated 5 minutes in 5 ml methanol, rinsed in 5 ml methanol) and then vacuum dried.

Peptide was removed from the resin by incubating 2 hours in reagent R and then precipitated into ether. Peptide was washed in ether and then vacuum dried. Peptide was resolubilized in $diH_2O$, frozen and lyophilized overnight.

Conjugation of Peptide with Keyhole Limpet Hemocyanin

Peptide (6 mg) was conjugated with Keyhole Limpet Hemocyanin (KLH). When the selected peptide included at least one cysteine, three aliquots (2 mg) were dissolved in PBS (2 ml) and coupled to KLH via glutaraldehyde, EDC or maleimide activated KLH (2 mg) in 2 ml of PBS for a total volume of 4 ml. When the peptide lacked cysteine, two aliquots (3 mg) were coupled via glutaraldehyde and EDC methods.

Maleimide coupling is accomplished by mixing 2 mg of peptide with 2 mg of maleimide-activated KLH dissolved in PBS (4 ml) and incubating 4 hr.

EDC coupling is accomplished by mixing 2 mg of peptide, 2 mg unmodified KLH, and 20 mg of EDC in 4 ml PBS (lowered to pH 5 by the addition of phosphoric acid), and incubating for 4 hours. The reaction is stopped by the slow addition of 1.33 ml acetic acid (pH 4.2). When using EDC to couple 3 mg of peptide, the amounts listed above are increased by a factor of 1.5.

Glutaraldehyde coupling occurs when 2 mg of peptide are mixed with 2 mg of KLH in 0.9 ml of PBS. 0.9 ml of 0.2% glutaraldehyde in PBS is added and mixed for one hour. 0.46 ml of 1 M glycine in PBS is added and mixed for one hour. When using glutaraldehyde to couple 3 mg of peptide, the above amounts are increased by a factor of 1.5.

The conjugated aliquots were subsequently repooled, mixed for two hours, dialyzed in 1 liter PBS and lyophilized.

Immunization of Rabbits

Two New Zealand White Rabbits were injected with 250 μg (total) KLH conjugated peptide in an equal volume of complete Freund's adjuvant and saline in a total volume of 1 ml. 100 μg KLH conjugated peptide in an equal volume of incomplete Freund's Adjuvant and saline were then injected into three to four subcutaneous dorsal sites for a total volume of 1 ml two, six, eight and twelve weeks after the first immunization. The immunization schedule was as follows:

| Day 0 | Pre-immune bleed, primary immunization |
| --- | --- |
| Day 15 | 1st boost |
| Day 27 | 1st bleed |
| Day 44 | 2nd boost |
| Day 57 | 2nd bleed and 3rd boost |
| Day 69 | 3rd bleed |
| Day 84 | 4th boost |
| Day 98 | 4th bleed |

Collection of Rabbit Serum

The rabbits were bled (30 to 50 ml) from the auricular artery. The blood was allowed to clot at room temperature for 15 minutes and the serum was separated from the clot using an IEC DPR-6000 centrifuge at 5000 g. Cell-free serum was decanted gently into a clean test tube and stored at −20° C. for affinity purification.

Determination of Antibody Titer

All solutions with the exception of wash solution were added by the Hamilton Eclipse, a liquid handling dispenser. The antibody titer was determined in the rabbits using an ELISA assay with peptide on the solid phase. Flexible high binding ELISA plates were passively coated with peptide diluted in BBS (100 μg/well) and the plate was incubated at 4° C. in a wetbox overnight (air-tight container with moistened cotton balls). The plates were emptied and then washed three times with BBS containing 0.1% Tween-20 (BBS-TW) by repeated filling and emptying using a semi-automated plate washer. The plates were blocked by completely filling each well with BBS-TW containing 1% BSA and 0.1% gelatin (BBS-TW-BG) and incubating for 2 hours at room temperature. The plates were emptied and sera of both pre- and post-immune serum were added to wells. The first well contained sera at 1:50 in BBS. The sera were then serially titrated eleven more times across the plate at a ratio of 1:1 for a final (twelfth) dilution of 1:204,800. The plates were incubated overnight at 4° C. The plates were emptied and washed three times as described.

Biotinylated goat anti-rabbit IgG (100 μl) was added to each microtiter plate test well and incubated for four hours at room temperature. The plates were emptied and washed three times. Horseradish peroxidase-conjugated Streptavidin (100 μl diluted 1:10,000 in BBS-TW-BG) was added to each well and incubated for two hours at room temperature. The plates were emptied and washed three times. The ABTS was prepared fresh from stock by combining 10 ml of citrate buffer (0.1 M at pH 4.0), 0.2 ml of the stock solution (15 mg/ml in water) and 10 μl of 30% hydrogen peroxide. The ABTS solution (100 μl) was added to each well and incubated at room temperature. The plates were read at 414 nm, 20 minutes following the addition of substrate.

Preparation of Peptide Affinity Purification Column:

The affinity column was prepared by conjugating 5 mg of peptide to 10 ml of cyanogen bromide-activated Sepharose 4B and 5 mg of peptide to hydrazine-Sepharose 4B. Briefly, 100 μl of DMF was added to peptide (5 mg) and the mixture was vortexed until the contents were completely wetted. Water was then added (900 μl) and the contents were vortexed until the peptide dissolved. Half of the dissolved peptide (500 μl) was added to separate tubes containing 10 ml of cyanogen-bromide activated Sepharose 4B in 0.1 ml of borate buffered saline at pH 8.4 (BBS) and 10 ml of hydrazine-Sepharose 4B in 0.1 M carbonate buffer adjusted to pH 4.5 using excess EDC in citrate buffer pH 6.0. The conjugation reactions were allowed to proceed overnight at room temperature. The conjugated Sepharose was pooled and loaded onto fitted columns, washed with 10 ml of BBS, blocked with 10 ml of 1 M glycine and washed with 10 ml 0.1 M glycine adjusted to pH 2.5 with HCl and re-neutralized in BBS. The column was washed with enough volume for the optical density at 280 nm to reach baseline.

Affinity Purification of Antibodies

The peptide affinity column was attached to a UV monitor and chart recorder. The titered rabbit antiserum was thawed and pooled. The serum was diluted with one volume of BBS and allowed to flow through the columns at 10 ml per minute. The non-peptide immunoglobulins and other proteins were washed from the column with excess BBS until the optical density at 280 nm reached baseline. The columns were disconnected and the affinity purified column was eluted using a stepwise pH gradient from pH 7.0 to 1.0. The elution was monitored at 280 nm and fractions containing antibody (pH 3.0 to 1.0) were collected directly into excess 0.5 M BBS. Excess buffer (0.5 M BBS) in the collection tubes served to neutralize the antibodies collected in the acidic fractions of the pH gradient.

The entire procedure was repeated with "depleted" serum to ensure maximal recovery of antibodies. The eluted material was concentrated using a stirred cell apparatus and a membrane with a molecular weight cutoff of 30 kD. The concentration of the final preparation was determined using an optical density reading at 280 nm. The concentration was determined using the following formula: $mg/ml = OD_{280}/1.4$.

It will be appreciated that in certain embodiments, additional steps may be used to purify antibodies of the invention. In particular, it may prove advantageous to repurify antibodies, e.g., against one of the peptides that was used in generating the antibodies. It is to be understood that the present invention encompasses antibodies that have been prepared with such additional purification or repurification steps. It will also be appreciated that the purification process may affect the binding between samples and the inventive antibodies.

Example 2

Preparing and Staining Tissue Arrays

This example describes a method that was employed to prepare the tissue arrays that were used in the Examples. This example also describes how the antibody staining was performed.

Tissue arrays were prepared by inserting full-thickness cores from a large number of paraffin blocks (donor blocks) that contain fragments of tissue derived from many different patients and/or different tissues or fragments of tissues from a single patient, into a virgin paraffin block (recipient block) in a grid pattern at designated locations in a grid. A standard slide of the paraffin embedded tissue (donor block) was then made which contained a thin section of the specimen amenable to H & E staining A trained pathologist, or the equivalent versed in evaluating tumor and normal tissue, designated the region of interest for sampling on the tissue array (e.g., a tumor area as opposed to stroma). A commercially available tissue arrayer from Beecher Instruments was then used to remove a core from the donor block which was then inserted into the recipient block at a designated location. The process was repeated until all donor blocks had been inserted into the recipient block. The recipient block was then thin-sectioned to yield 50-300 slides containing cores from all cases inserted into the block.

The selected antibodies were then used to perform immunohistochemical staining using the DAKO Envision+, Peroxidase IHC kit (DAKO Corp., Carpenteria, Calif.) with DAB substrate according to the manufacturer's instructions.

Example 3

Correlating Interaction Partner Binding with Clinical Prognostic Data in HER2+ Breast Cancer This example describes the identification of the HTF9C marker as a strong prognosticator for HER2+ breast cancer patients.

Tissue microarrays from two previously established breast cancer cohorts (CCIH and CCF, see Ring et al., "Novel Prognostic Immunohistochemical Marker Panel for Estrogen Receptor-Positive Breast Cancer", *J. Clin. Oncol.* 24:3039-47, 2006, see also Table 1) were used to investigate potential IHC markers to help stratify HER2+ breast cancer patients into different prognostic categories. Clinical information for the patients within both cohorts included recurrence at 5 years. The patients in both cohorts were not treated with Trastuzumab (Herceptin™) before the recurrence event (if at all).

Tissue samples for the patients in the CCIH cohort were stained with 37 antibodies selected from the list in Appendix A. A rabbit monoclonal antibody to the HTF9C marker (s0722, prepared according to Example 1 using the same peptide as the polyclonal antibody s0545, see Appendix A) showed strong univariate association with likelihood of recurrence at 5 years within 67 HER2+ patients from the CCIH cohort (HR 6.98; 95% CI 2.42 to 20.10, p<0.0004). HTF9C stained cases showed a strong uniform granular cytoplasmic staining of tumor cells. Occasional cases show some staining of nuclei which was ignored for the purpose of assessing staining with HTF9C. Nodal status but not tumor size was associated with outcome in HER2 expressing patients in this cohort (Table 2).

This prognostic correlation was validated on 75 HER2+ patients from the CCF cohort (HR 3.62; 95% CI 1.28 to 10.20, p<0.02). We subsequently assessed all 37 of the original antibodies that were tested on the CCIH cohort and found that in the CCF cohort both estrogen receptor and progesterone receptor expression were also associated with outcome. Neither pathologic nor clinical stage was associated with outcome in this cohort (Table 2).

The prognostic value of the HTF9C marker was also assessed by generating Kaplan-Meier recurrence curves for the HER2+ patients in the two cohorts. Patients whom the panels predicted as being likely to recur were placed in the "poor" prognosis group. Patients whom the panels predicted as being unlikely to recur were given the prediction of "good". Kaplan-Meier curves were then calculated based on recurrence data for patients within each group and are shown in FIG. 4.

FIG. 4 also shows the curves that were obtained when the same patients were classified based on staining for the ER marker. As previously noted, the ER marker is anti-correlated with the HTF9C marker in HER2+ patients (i.e., staining for ER is associated with good outcome while staining for HTF9C is associated with poor outcome). The correlation was good in the CCF cohort (HR 0.263; 95% CI 0.107 to 0.649, p<0.005) but poor in the CCIH cohort (HR 0.53; 95% CI 0.212 to 1.32, p<0.170). These results agree with the mixed reputation of the ER marker as an individual prognosticator in HER2+ patients.

A third breast cancer cohort from the Roswell Park Institute (RP) was assembled to test the association identified and confirmed in the CCIH and CCF cohorts respectively. The RP cohort was assembled by retrospective review of the pathology archives over a 10 year period to identify HER2+ breast cancer patients who where 3+ positive by immunohistochemistry using the Herceptest™ test kit (Dako, Carpenteria, Calif.). HER2 IHC status for all 64 cases identified was confirmed by re-staining. The clinicopathologic characteristics for RP patient cohort are compared with those from the CCIH and CCF cohorts in Table 1.

TABLE 1

Clinical and Pathologic Features of Cohorts

|  |  | CCIH | | CCF | | RP |
| --- | --- | --- | --- | --- | --- | --- |
|  |  | Total | Her2 | Total | Her2 | Her2 |
| Number |  | 496 | 69 | 299 | 75 | 64 |
| ER | + | 323 | 38 | 195 | 54 | 32 |
|  | − | 144 | 31 | 51 | 19 | 28 |
|  | Unknown | 29 | 0 | 53 | 2 | 4 |
| PR | + | 245 | 20 | 118 | 27 | 10 |
|  | − | 215 | 48 | 134 | 45 | 46 |
|  | Unknown | 36 | 1 | 47 | 3 | 8 |
| Age | Mean | 58 | 56 | 62 | 59 | 56 |
|  | <50 | 140 | 25 | 74 | 25 | 23 |
|  | ≥50 | 356 | 44 | 225 | 50 | 41 |
| N Stage | 0 | 291 | 34 | 170 | 47 | 23 |
|  | 1 | 187 | 32 | 68 | 15 | 31 |
|  | 2 | 9 | 3 | 12 | 10 | 5 |
|  | 3 | 0 | 0 | 0 | 2 | 3 |
|  | Unknown | 9 | 0 | 25 | 1 | 2 |
| T Stage | 1 | 237 | 26 | 167 | 40 | 29 |
|  | 2 | 179 | 35 | 96 | 25 | 22 |
|  | 3 | 22 | 2 | 19 | 4 | 5 |
|  | 4 | 12 | 4 | 13 | 5 | 5 |
|  | Unknown | 46 | 2 | 4 | 1 | 3 |
| Grade | 1 | 69 | 5 | 45 | 7 | 4 |
|  | 2 | 175 | 21 | 120 | 32 | 22 |
|  | 3 | 162 | 32 | 83 | 31 | 35 |
|  | Unknown | 90 | 11 | 51 | 5 | 3 |
| Chemo | None | 250 | 28 | 145 | 31 | 18 |
|  | Standard Adjuvant | 241 | 41 | 93 | 22 | 45 |
|  | Unknown | 5 | 0 | 60 | 22 | 1 |

Within the RP cohort, only tumor grade was associated with outcome while estrogen receptor, progesterone receptor, nodal status, stage, and treatment with cytotoxic chemotherapy were not. The same rabbit monoclonal antibody to the HTF9C marker (s0722, prepared according to Example 1 using the same peptide as s0545 shown in Appendix A) was used to stain the TMA samples. Cytoplasmic staining correlated with disease recurrence (HR 3.42; 95% CI 1.3-8.9, p<0.02). By multivariate analysis, HTF9C was significantly associated with outcome when combined individually with each clinical and pathological variables with the exception of estrogen receptor expression which was near significant (p=0.066) (Table 2).

In the three institutional cohorts, HTF9C stained 29%, 37% and 23% of the CCIH, CCF and RP patients respectively, however, these subsets of patients contained 69%, 59% and 47% of the total number of HER2+ patients that recurred respectively. With the CCIH and CCF cohorts, where comparison with HER2− patients was possible, the five year recurrence rate of HER2+/HTF9C− was lower than that of HER2− patients (CCIH: 10% versus 19%, CCF: 12% versus 17%).

It is to be understood that interaction partners for the HTF9C marker may be used in a prognostic panel that includes interaction partners for other markers. In particular, a panel that includes interactions partners for the HTF9C marker and the ER marker is expected to provide useful prognostic information. In general, it is to be understood that any interaction partner could be added to such a panel. Without limitation, one could use interaction partners against any of the markers that are listed in Appendix A. These prognostic panels could be constructed using any method. Without limitation these include simple empirically derived rules, Cox multivariate proportional hazard models (e.g., see Cox and Oakes, "Analysis of Survival Data", Chapman & Hall, 1984), regression trees (e.g., see Segal and Bloch, *Stat. Med.* 8:539-50, 1989), and/or neural networks (e.g., see Ravdin et al., Breast Cancer Res. Treat. 21:47-53, 1992). When antibodies are used as interaction partners, then in certain embodiments a prognostic panel might include an antibody against the HTF9C marker and between 1-9 other antibodies (e.g., an antibody against the ER marker), for example 2-8, 4-6 or 3-5 other antibodies. It will be appreciated that these ranges are exemplary and non-limiting.

TABLE 2

|  |  | Univariate | Bivariate Factor | HTF9C | Univariate | Bivariate Factor | HTF9C |
|---|---|---|---|---|---|---|---|
|  |  | CCIH | | | CCF | | |
| ER | HR | 0.435 | 1.05 | 7.15 | 0.294 | 0.234 | 1.412 |
|  | P | 0.11 | 0.93 | 0.0012 | 0.015 | 0.045 | 0.64 |
| PR | HR | 0.347 | 1.04 | 7.08 | 0.205 | 0.143 | 2.711 |
|  | P | 0.16 | 0.97 | 0.0024 | 0.036 | 0.067 | 0.082 |
| Age | HR | 1.01 | 1.01 | 6.91 | 0.982 | 0.974 | 3.47 |
|  | P | 0.52 | 0.61 | 0.00035 | 0.3 | 0.15 | 0.019 |
| N Stage | HR | 4.16 | 3.9 | 5.63 | 2.47 | 2.41 | 2.03 |
|  | P | 0.00043 | 0.0027 | 0.0015 | 0.0001 | 0.0002 | 0.23 |
| T Stage | HR | 1.2 | 1.07 | 6.93 | 2.34 | 2.72 | 2.31 |
|  | P | 0.54 | 0.85 | 0.00046 | 0.0001 | 0.0001 | 0.13 |
| Grade | HR | 0.869 | 0.805 | 12.25 | 2.16 | 2.35 | 2.8 |
|  | P | 0.74 | 0.59 | 0.00018 | 0.079 | 0.091 | 0.057 |
| Chemo | HR | 1.64 | 0.925 | 7.14 | 8.78 | 15.13 | 2.23 |
|  | P | 0.36 | 0.925 | 0.89 | 0.0048 | 0.0098 | 0.17 |
|  |  | RP | | | CCF & RP | | |
| ER | HR | 0.471 | 0.573 | 2.573 | 0.358 | 0.364 | 2.015 |
|  | P | 0.13 | 0.3 | 0.066 | 0.0032 | 0.014 | 0.08 |
| PR | HR | 0.18 | 0 | 2.8 | 0.192 | 0.0869 | 2.5323 |
|  | P | 0.1 | 0.73 | 0.058 | 0.0065 | 0.017 | 0.015 |
| Age | HR | 1 | 1 | 3.39 | 0.991 | 0.985 | 3.386 |
|  | P | 0.87 | 0.85 | 0.013 | 0.42 | 0.26 | 0.0006 |
| N Stage | HR | 1.17 | 1.37 | 3.33 | 1.84 | 1.98 | 2.78 |
|  | P | 0.52 | 0.3 | 0.014 | 0 | 0 | 0.0047 |
| T Stage | HR | 1.24 | 1.14 | 3.35 | 1.77 | 1.78 | 3.06 |
|  | P | 0.26 | 0.56 | 0.014 | 0 | 0.00032 | 0.0018 |
| Grade | HR | 3.5 | 2.96 | 3.34 | 2.71 | 2.68 | 2.93 |
|  | P | 0.018 | 0.077 | 0.017 | 0.0026 | 0.01 | 0.0032 |
| Chemo | HR | 1.46 | 1 | 3.34 | 2.97 | 2.96 | 2.46 |
|  | P | 0.42 | 0.99 | 0.014 | 0.007 | 0.02 | 0.02 |

Example 4

Correlating Interaction Partner Binding with Response to Therapy Data in HER2+ Breast Cancer According to the present invention, interaction partners (e.g., antibodies) for the HTF9C marker are tested for their ability to predict response to therapy in HER2+ breast cancer patients. Samples from one or more cohorts of HER2+ breast cancer patients for which clinical response information is known (or being monitored) are stained with the interaction partners. Staining patterns are then correlated with response to therapy to identify strong correlations. Exemplary therapies include HER2 targeted agents including Trastuzumab (Herceptin™); HER family targeted agents (EGFR/HER1, HER3, HER4); cytotoxic agents and combinations of these. Indeed, some of the HER family members heterodimerize with HER2 thereby creating an opportunity to target HER2 though the dimer. In addition, cytotoxic chemotherapy has been shown to be more effective in HER2+ patients in terms of relative improvement.

Optionally, the staining of HTF9C is combined with the straining of other markers (e.g., any of those in Appendix A) to identify panels with staining patterns that correlate strongly with response to therapy. In particular, the combination of HTF9C and ER staining is analyzed.

Example 5

Correlating Interaction Partner Binding with Outcome/Responsiveness of Xenograft Tumors According to the present invention, panels of useful interaction partners may be defined through analysis of human tumor cells grown in a non-human host. In particular, such analyses may define interaction partner panels whose binding correlates with prognosis and/or with responsiveness to therapy.

Cells derived from human tumors may be transplanted into a host animal (e.g., a mouse), preferably into an immunocompromised host animal. In preferred embodiments of the invention, cells (e.g., cell lines, tumor samples obtained from human patients, etc.) from a variety of different human tumors (e.g., at least 10, 20, 30, 40, 50, 60 or more different tumors) are transplanted into host animals. The animals are then treated with different (e.g., increasing) concentrations of a chemical compound known or thought to be selectively toxic to tumors with a predetermined common characteristic (e.g., class or subclass). Relative growth or regression of the tumors may then be assessed using standard techniques.

In certain embodiments of the invention, a dataset of sensitivity of the transplanted cells to a given compound or set of compounds may optionally be created. For example, a dataset might consist of the concentration of compound administered to the host animal that inhibited tumor growth 50% at 96 hr (i.e., the $LD_{50}$) for each of the cell samples or cell lines tested. Such a dataset, for example across at least 10, 20, 30, 40, 50, 60 or more cell lines, could then be correlated with the relative staining of the binding partners across the same cell lines. Those binding partners whose interaction (or lack thereof)

with cells was highly correlated with either sensitivity to or resistance to a given compound would be useful members of a predictive panel.

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

We claim:

1. A method comprising steps of:
obtaining a tumor sample from a patient having an HER2+ breast tumor;
contacting the tumor sample with a first antibody directed to HTF9C (HpaII tiny fragments locus 9C); and
assessing the patient's likely prognosis based upon binding of the first antibody to the tumor sample, wherein binding of the first antibody correlates with a higher likelihood that the patient will have a poor outcome.

2. The method of claim 1 further comprising:
providing a positive control sample; and
contacting the positive control sample with a first antibody directed to HTF9C (HpaII tiny fragments locus 9C), wherein the step of assessing the patient's likely prognosis comprises a step of comparing the binding of the first antibody to the tumor sample with the binding of the first antibody to the positive control sample.

3. The method of claim 1, wherein the first antibody is a monoclonal antibody.

4. The method of claim 1 further comprising:
determining from the binding of the first antibody that the patient's prognosis is poor and administering a breast cancer therapeutic to the patient.

5. The method of claim 4, wherein the breast cancer therapeutic is Trastuzumab.

6. The method of claim 1 further comprising:
confirming the breast tumor is positive for HER2.

7. The method of claim 6, wherein the breast tumor is confirmed to be positive for HER2 by imunohistochemistry.

8. The method of claim 6, wherein the breast tumor is confirmed to be positive for HER2 by in situ hybridization.

9. The method of claim 1 further comprising:
contacting the tumor sample with a second antibody directed to estrogen receptor, wherein in the step of assessing, the patient's likely prognosis is assessed based upon binding of the first and second antibodies to the tumor sample, wherein binding of the second antibody correlates with a higher likelihood that the patient will have a good outcome.

10. The method of claim 9, wherein binding of the second antibody correlates with a lower likelihood that the patient will have a recurrence.

11. The method of claim 9, wherein binding of the second antibody correlates with a higher likelihood that the patient will survive for a period of time.

12. The method of claim 1, wherein binding of the first antibody correlates with a higher likelihood that the patient will have a recurrence.

13. The method of claim 1, wherein binding of the first antibody correlates with a lower likelihood that the patient will survive for a period of time.

14. A method comprising steps of:
obtaining a tumor sample from a patient having an HER2+ breast tumor;
contacting the tumor sample with a first antibody directed to HTF9C (HpaII tiny fragments locus 9C); and
classifying the HER2+ breast tumor based upon binding or nonbinding of the first antibody to HTF9C (HpaII tiny fragments locus 9C) in the tumor sample.

15. The method of claim 14 further comprising:
contacting the tumor sample with a second antibody directed to estrogen receptor, wherein in the step of classifying, the HER2+ breast tumor is classified based upon binding or nonbinding of the first antibody to HTF9C (HpaII tiny fragments locus 9C) in the tumor sample and based on binding or nonbinding of the second antibody to estrogen receptor in the tumor sample.

* * * * *

UNITED STATES PATENT AND TRADEMARK OFFICE
CERTIFICATE OF CORRECTION

PATENT NO. : 8,697,373 B2  Page 1 of 1
APPLICATION NO. : 12/444007
DATED : April 15, 2014
INVENTOR(S) : Ring et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1232 days.

Signed and Sealed this

Twenty-ninth Day of September, 2015

Michelle K. Lee
*Director of the United States Patent and Trademark Office*